United States Patent [19]
Johnson et al.

[11] Patent Number: 5,394,732
[45] Date of Patent: Mar. 7, 1995

[54] METHOD AND APPARATUS FOR ULTRASONIC DETECTION OF AIR BUBBLES

[75] Inventors: David A. Johnson, Littleton; Douglas P. Miller, Broomfield; Keith J. Manica, Lakewood; William M. Dormont, Boulder; Christopher J. Welsh, Fort Collins, all of Colo.; William R. Mandel, Harlem, Mont.

[73] Assignee: COBE Laboratories, Inc., Lakewood, Colo.

[21] Appl. No.: 119,790

[22] Filed: Sep. 10, 1993

[51] Int. Cl.⁶ ............................................. G01N 29/02
[52] U.S. Cl. .................................. 73/19.1; 73/19.03; 73/600
[58] Field of Search ............... 73/19.03, 19.1, 61.75, 73/61.79, 599, 600

[56] References Cited

U.S. PATENT DOCUMENTS

| | | |
|---|---|---|
| 2,755,662 | 7/1956 | Swengel . |
| 2,885,887 | 5/1959 | Hanysz ................................. 73/600 |
| 2,949,769 | 8/1960 | Heller . |
| 3,392,574 | 7/1968 | Lemon et al. . |
| 3,443,433 | 5/1969 | Liston et al. . |
| 3,641,994 | 2/1972 | Gosling et al. . |
| 3,881,353 | 5/1975 | Fathauer . |
| 3,914,984 | 10/1975 | Wade . |
| 3,921,622 | 11/1975 | Cole . |
| 3,974,681 | 8/1976 | Namery . |
| 3,974,683 | 8/1976 | Martin . |
| 4,014,206 | 3/1977 | Taylor ................................. 73/19.1 |
| 4,015,464 | 4/1977 | Miller et al. . |
| 4,022,058 | 5/1977 | Brown . |
| 4,068,521 | 1/1978 | Cosentino et al. . |
| 4,102,655 | 7/1978 | Jeffery et al. . |
| 4,112,773 | 9/1978 | Abts ................................. 73/19.1 X |
| 4,121,094 | 10/1978 | DiVito et al. . |
| 4,122,713 | 10/1978 | Staaz et al. . |
| 4,137,940 | 2/1979 | Faisandier . |
| 4,202,049 | 5/1980 | Wetzel . |
| 4,341,116 | 7/1982 | Bilstad et al. . |
| 4,418,565 | 12/1983 | St. John . |
| 4,487,601 | 12/1984 | Lindemann . |
| 4,607,520 | 8/1986 | Dam . |
| 4,651,555 | 3/1977 | Dam . |
| 4,666,598 | 5/1987 | Heath et al. . |
| 4,673,927 | 6/1987 | Cianciavicchia et al. ....... 73/19.1 X |
| 4,681,606 | 7/1987 | Swan et al. . |
| 4,722,224 | 2/1988 | Scheller et al. ................. 73/600 |
| 5,177,993 | 1/1993 | Beckman et al. ................ 73/19.03 |
| 5,191,795 | 3/1993 | Fellingham et al. . |

FOREIGN PATENT DOCUMENTS

| | | | |
|---|---|---|---|
| 107756 | 5/1991 | Japan | .................. 73/19.1 |
| 107758 | 5/1991 | Japan | .................. 73/19.1 |
| 838552 | 6/1981 | U.S.S.R. | .................. 73/19.03 |

Primary Examiner—Hezron E. Williams
Assistant Examiner—Joseph W. Roskos
Attorney, Agent, or Firm—Bruce R. Winsor

[57] ABSTRACT

Inclusions in a liquid flow, such as air bubbles in a blood flow, are detected by transmitting a signal through the fluid and receiving and interpreting the received signal based on the expected degree of attenuation for the liquid and the inclusions. The amplitude of the transmitted signal is automatically adjusted to maintain a constant average amplitude of the detected signal, thus compensating for changes in the detection environment. The average amplitude of the transmitted signal is controlled by integrating the received signal using an integrator with a time constant longer than the time constant of the expected inclusion signals, and comparing the integrated signal to a constant reference level.

The presence of microbubbles is detected and a signal comprising a string of high frequency pulses is generated while the microbubbles are present. By counting the pulses, in conjunction with knowledge about the flow of liquid and the anticipated size of the microbubbles, an estimate of the total amount of air infused into the patient within a given time period is calculated.

A tubing holder for retaining a flexible tube in an inclusion detector has tubing retention grooves formed into tubing engagement faces, the tubing engagement faces being spaced closer together than the tube diameter. The tube is inserted into the tubing holder by compressing and deforming it against the tubing engagement faces, until it reaches the tubing retaining grooves.

45 Claims, 17 Drawing Sheets

Fig_3

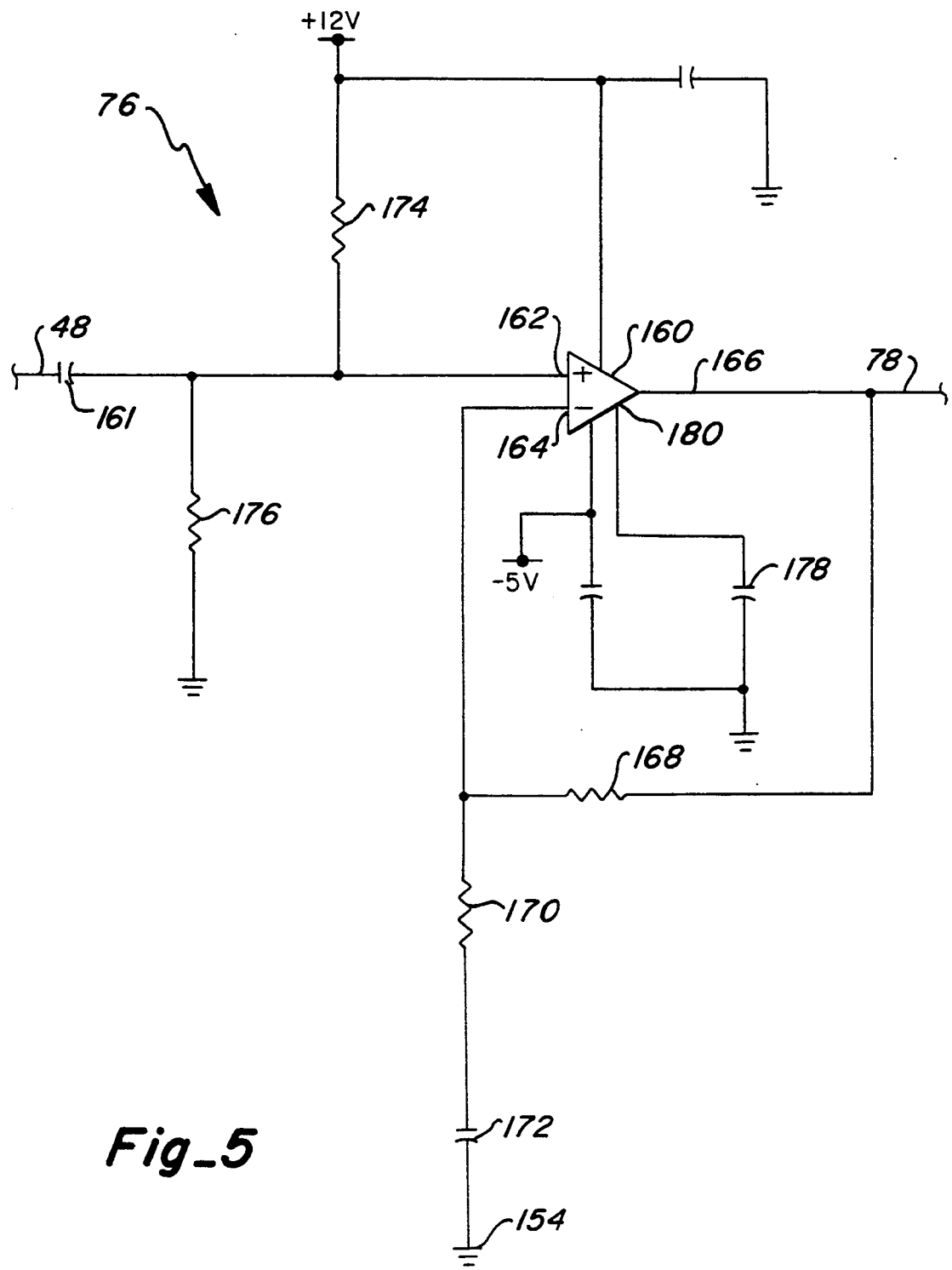
Fig_5

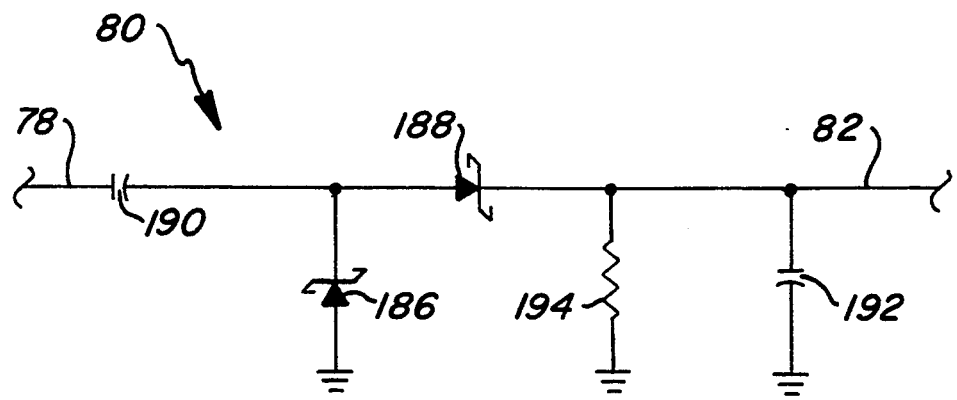
*Fig_6*
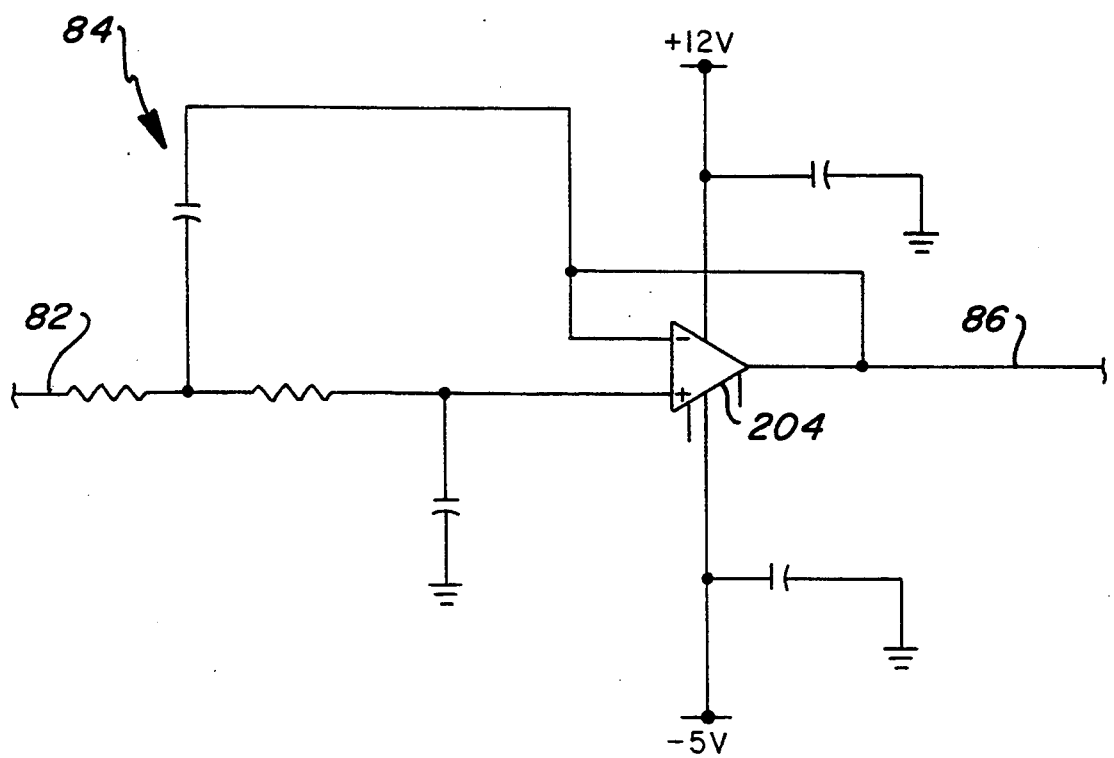
*Fig_7*

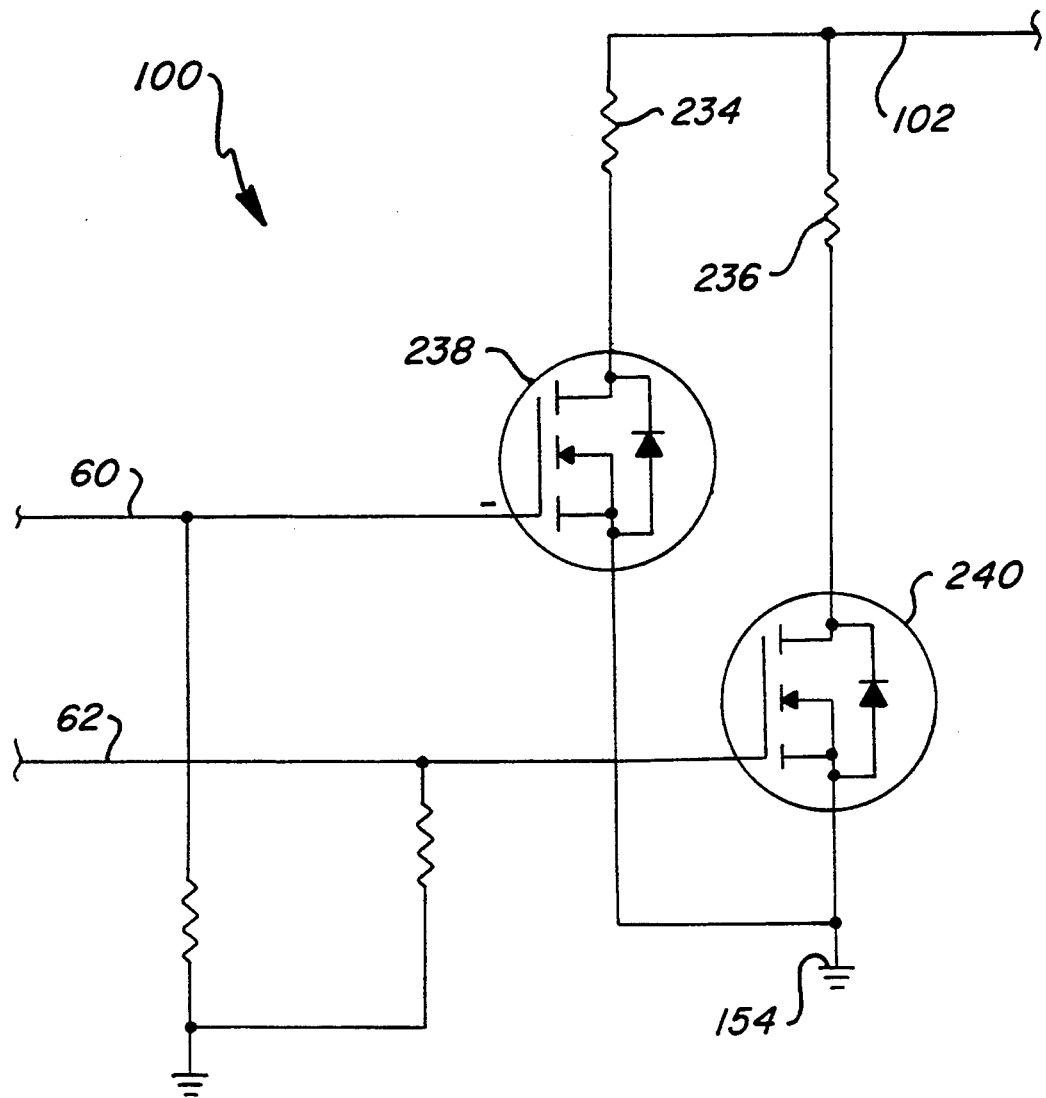
Fig_9

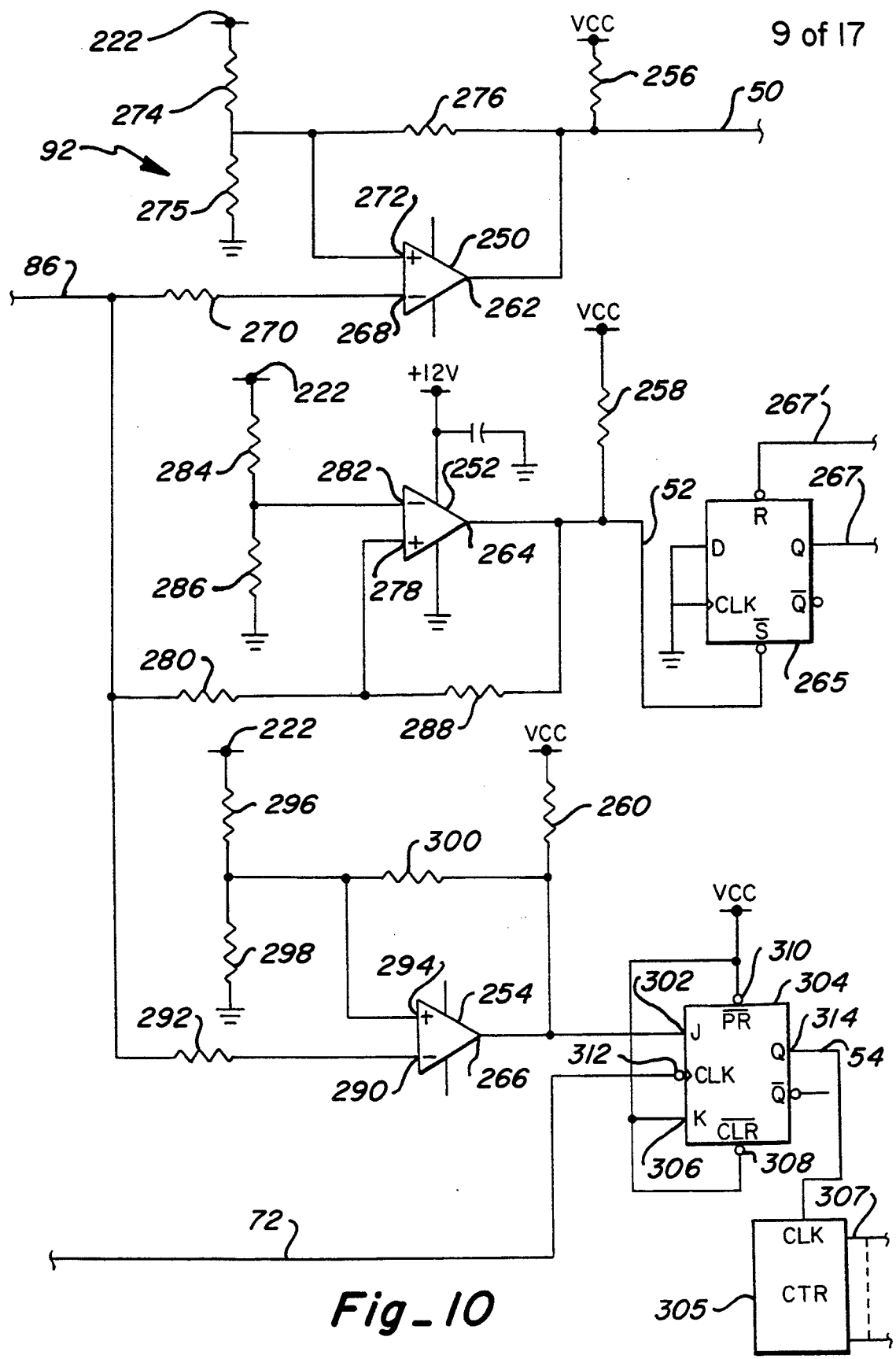
Fig_10

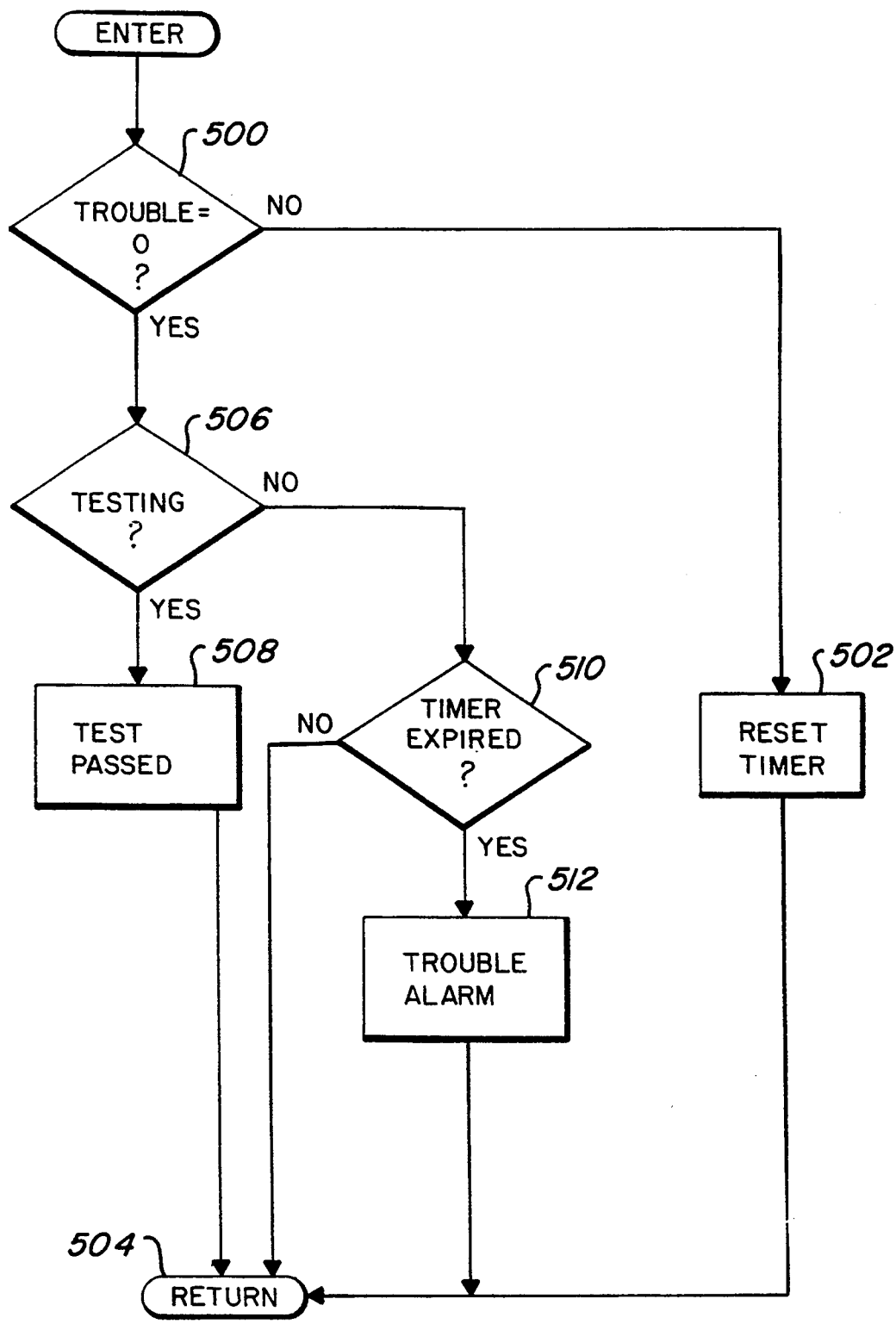
Fig_11

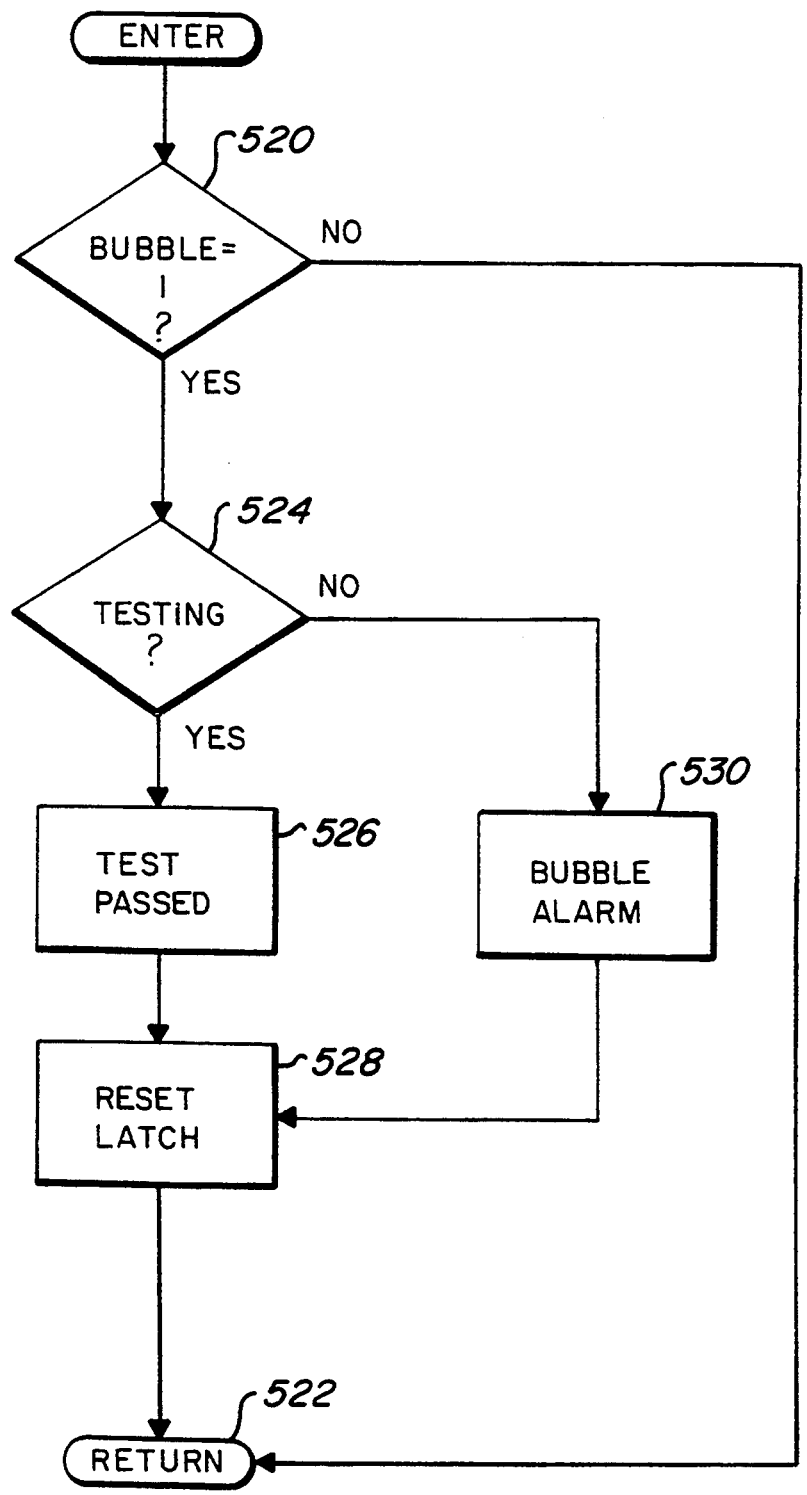
Fig_12

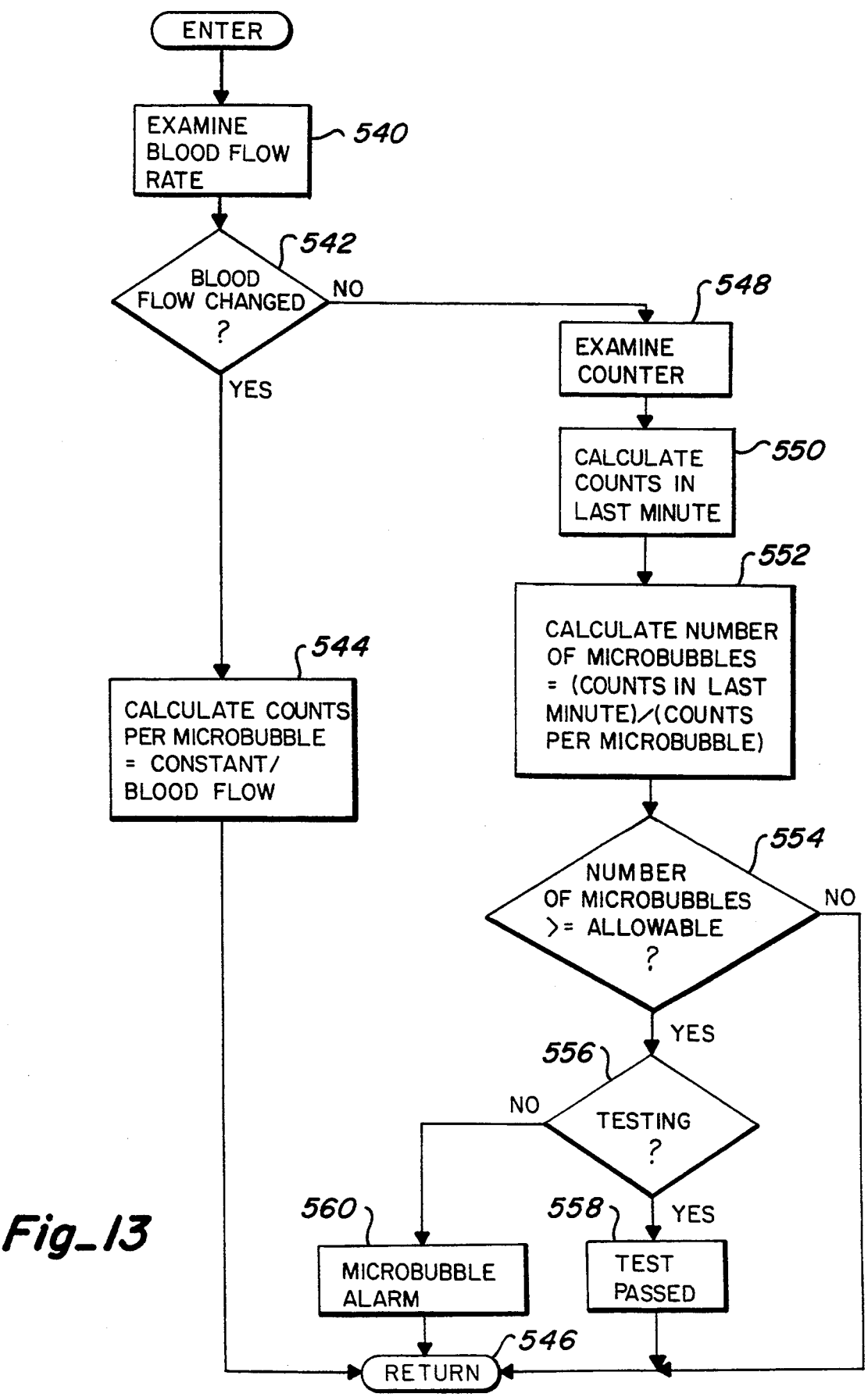
Fig_13

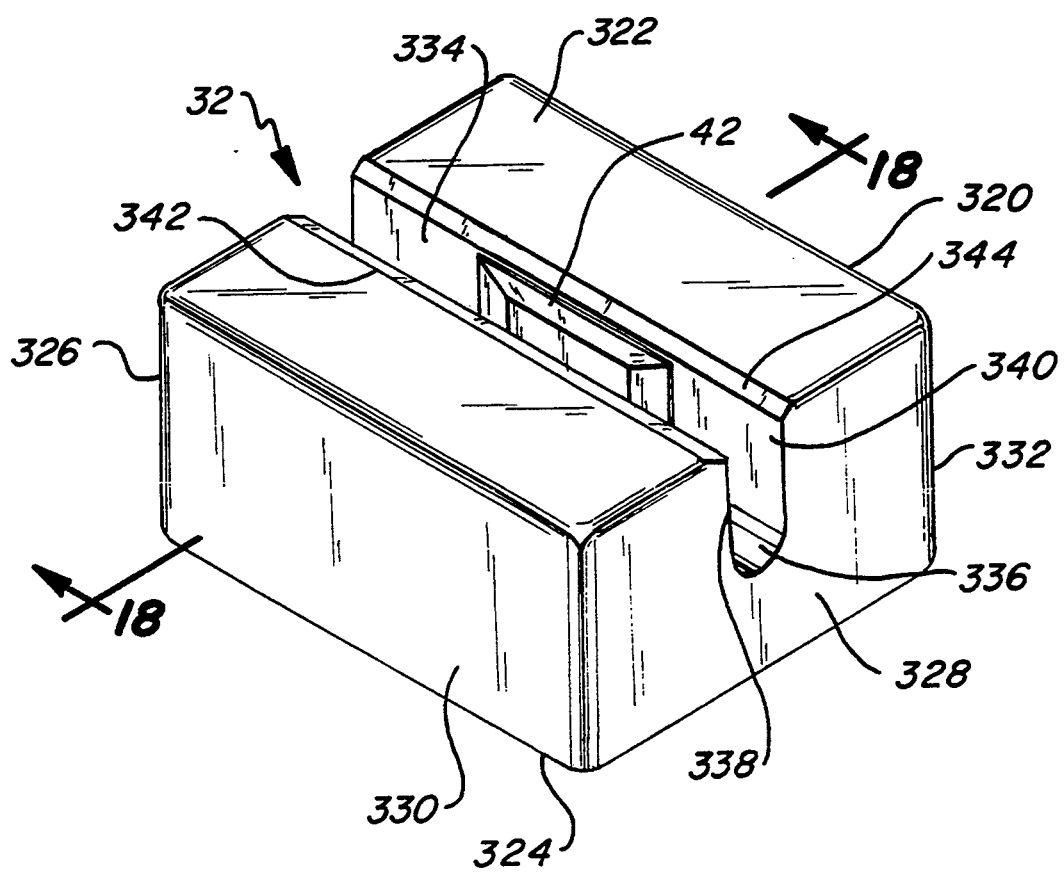
Fig_14

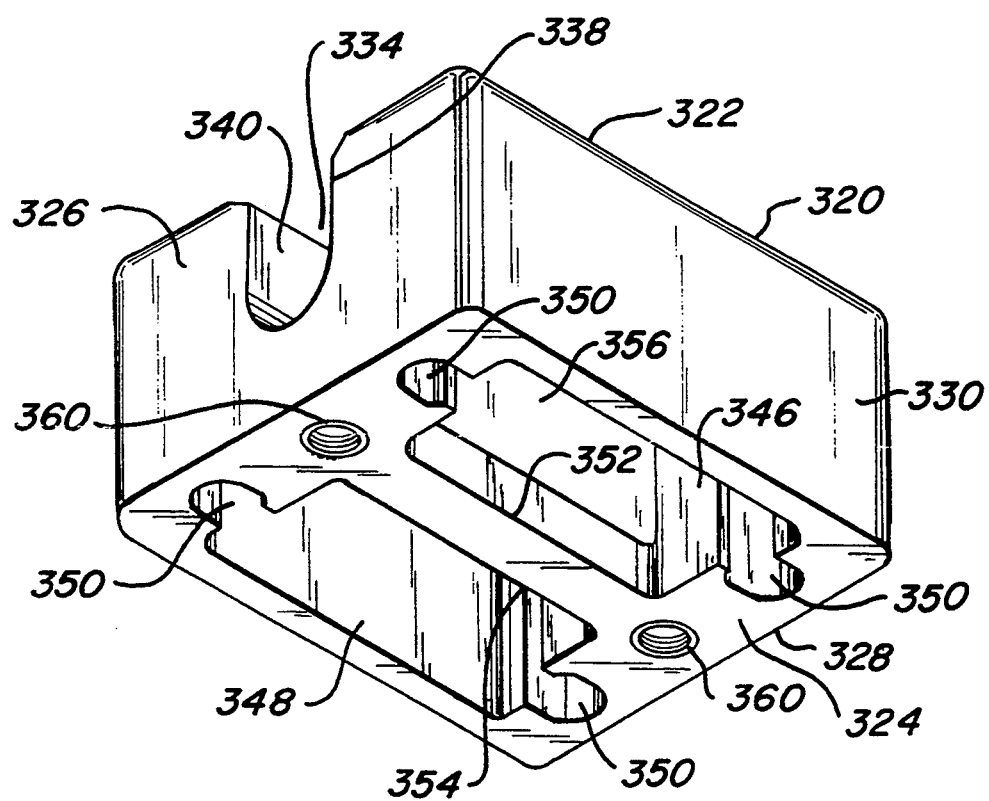
Fig _ 15

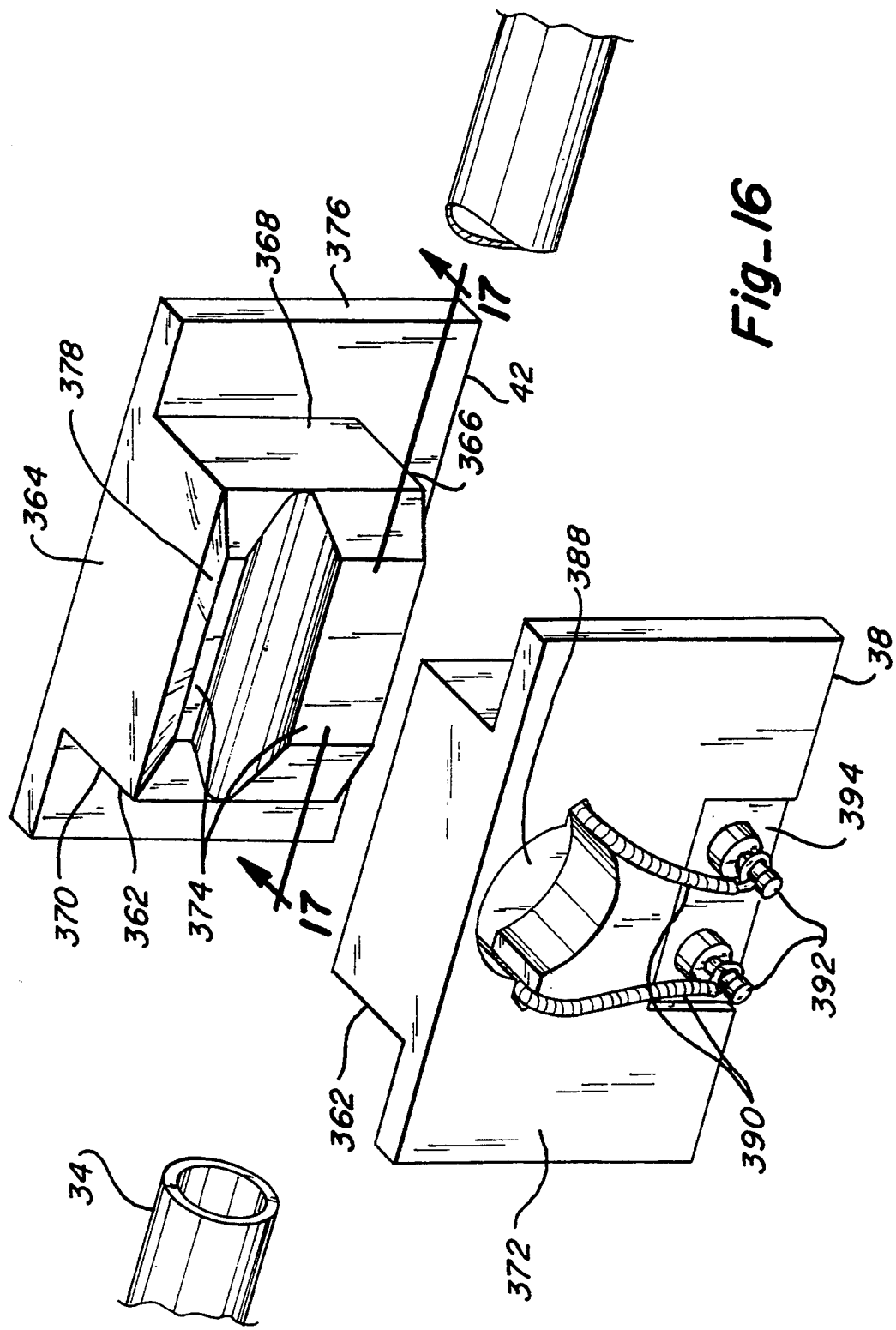
Fig_16

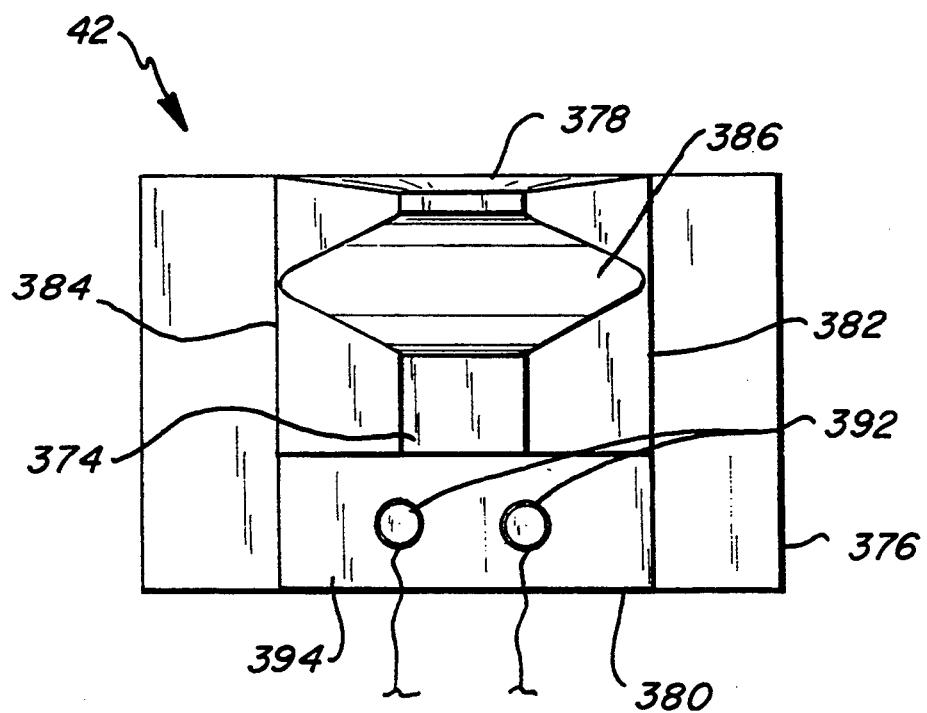
Fig_17

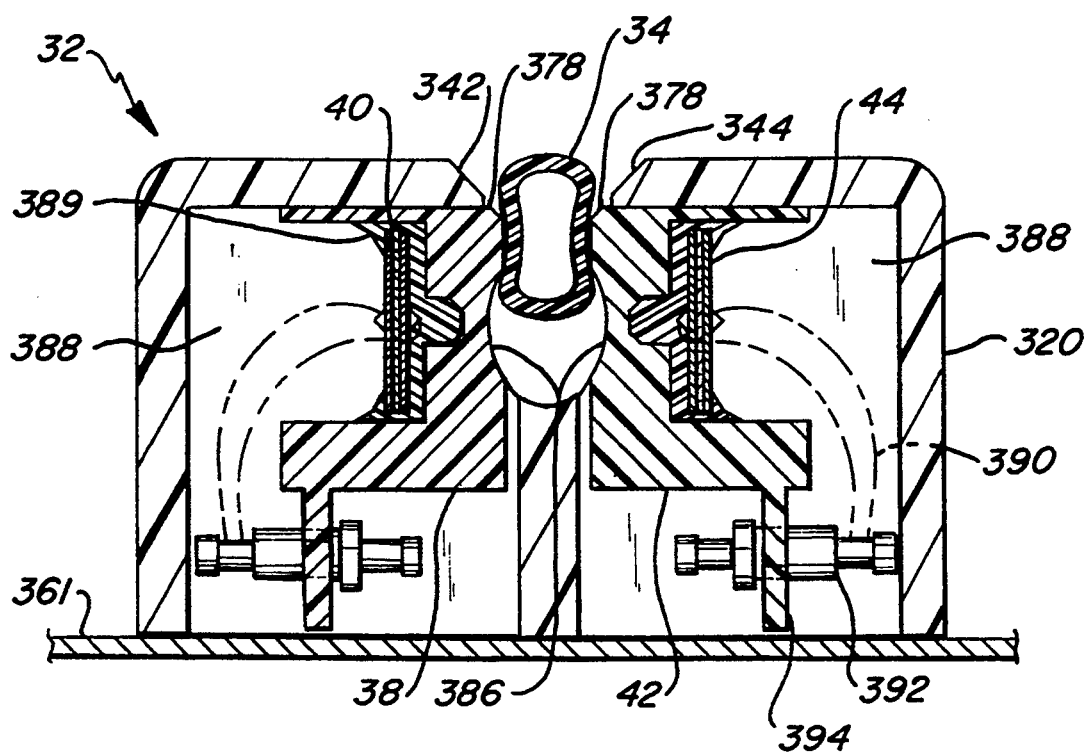
Fig_18
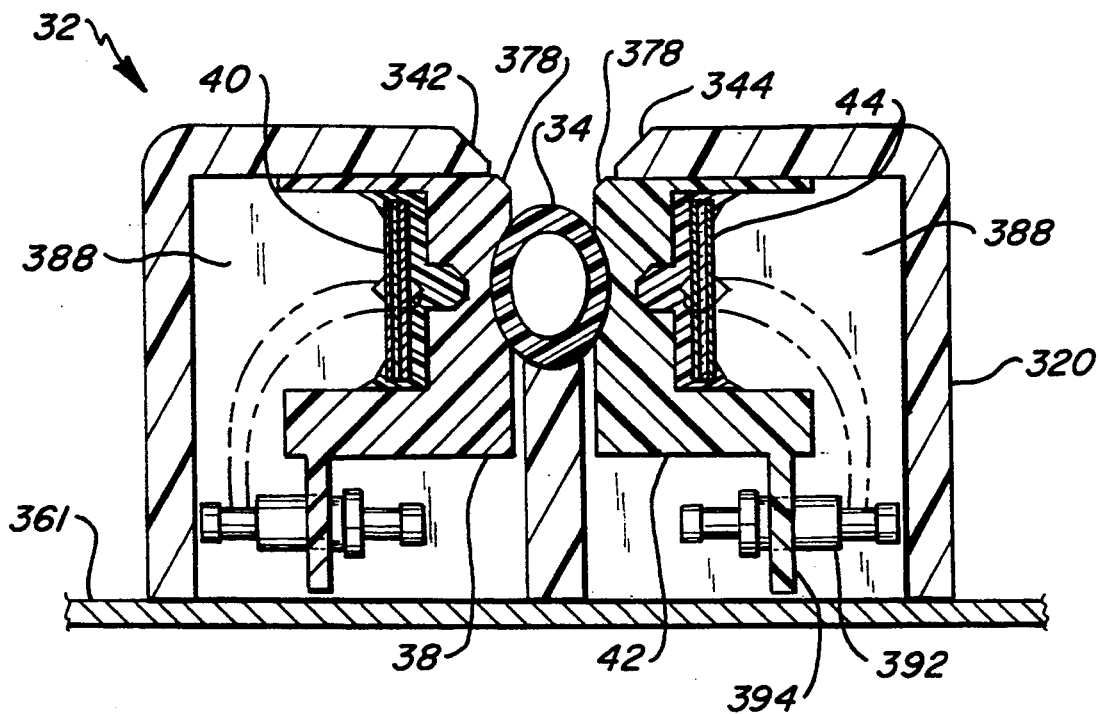
Fig_19

METHOD AND APPARATUS FOR ULTRASONIC DETECTION OF AIR BUBBLES

This invention relates to the detection of inclusions in liquids. More particularly this invention relates to the detection of air and gas bubbles in biological or pharmaceutical liquids such as blood.

BACKGROUND OF THE INVENTION

An artificial kidney apparatus is an extracorporeal blood circulation and processing system in which blood is removed from a patient, dialyzed to remove impurities and excess liquid, and returned to the patient.

In chronic care dialysis the patient typically is suffering from long term or end stage renal failure. Although the chronic care dialysis patient is quite ill, the patient's condition is usually relatively stable. The chronic patient typically visits a dialysis center periodically, approximately two or three times a week, to be dialyzed. Blood flows and amounts of fluids and impurities removed are relatively large and removed over a relatively short time. Acute care dialysis is more typical of temporary renal failure, such as from trauma. Under these circumstances the patient's body is often unable to withstand the relatively drastic and sudden changes that accompany chronic care dialysis. It is, therefore, desirable to dialyze the patient continuously at very low blood flow rates.

An objective common to virtually all extracorporeal circulation and processing systems for biological liquids, such as blood, and to infusion of biological liquids, such as blood or blood components, and pharmaceutical liquids, such as saline solution and intravenous medications, is to minimize or eliminate the infusion of undissolved air or gases (referred to simply as "air" hereafter) into the body of the patient. The air may take the form of fairly large bubbles or may be in the form of much smaller bubbles referred to as microbubbles. It is well known that the infusion of large bubbles of air can result in injury or death to the patient. The effects of a small number of microbubbles are less serious, but it is generally considered prudent to limit the total amount or rate of air infused in the form of microbubbles.

In chronic care dialysis air is typically removed and detected in a drip chamber located in a return line to the patient. The drip chamber is a relatively large volume reservoir with an air-blood interface configured to induce air bubbles to coalesce and leave the blood at the air-blood interface. Exemplary drip chambers are illustrated in U.S. Pat. No. 4,102,655 issued in 1978 to Jeffery et al., U.S. Pat. No. 4,666,598 issued in 1987 Heath et. al., and U.S. Pat. No. 4,681,606 issued in 1987 to Swan, Jr., et al. The possibility of infusing air into the patient is relatively easy to detect in a drip chamber because a build up of air will cause the level of blood in the chamber to drop. Necessary protective measures can be initiated when the blood level in the drip chamber drops below a predetermined level.

In acute care dialysis the blood flow rate through the artificial kidney apparatus is much lower than in typical chronic care dialysis. In acute care dialysis it is disadvantageous to use a drip chamber because of an increased possibility of blood clot formation due to low blood velocity and the presence of the air-blood interface. In order to detect bubbles at these low blood flow rates it is desirable to detect them directly in the tubing of the line that returns treated blood to the patient, rather than using a drip chamber. Of course, tubing type air bubble detectors may also be used advantageously in conjunction with chronic care dialysis artificial kidney apparatus and in any other situation where it is desired to detect the passage of air, such as in conjunction with the infusion of a pharmaceutical liquid or a biological liquid. Tubing type air bubble detectors may further be used advantageously in conjunction with blood apheresis and cardiovascular bypass procedures.

Furthermore, because acute care dialysis is continuous, the cumulative effects of microbubbles, while not well understood, may be more important in acute care dialysis than in chronic care dialysis.

Air detectors typically comprise a transmitting means and a receiving means. The transmitting means transmits a signal, such as an ultrasonic signal, through a chamber or tubing. The receiving means detects the signal and interprets it. The liquid and inclusions attenuate the signals differently. For example, blood and other liquids attenuate ultrasonic signals relatively little, while air and other gases attenuate ultrasonic signals relatively greatly. By monitoring the degree of attenuation of the ultrasonic signal as it passes through the chamber or tubing, it is possible to interpret a decrease in the strength of the signal received by the receiving means as indicative of the presence of a bubble. Ultrasonic air bubble detectors (UABDs) are described generally in U.S. Pat. No. 3,921,622 issued in 1975 to Cole, 3,974,681 issued in 1976 to Namery, U.S. Pat. No. 4,068,521 issued in 1978 to Consentino et al., U.S. Pat. No. 4,341,116 issued in 1982 to Bilstad et al., U.S. Pat. No. 4,418,565 issued in 1983 to St. John, U.S. Pat. No. 4,487,601 issued in 1984 to Lindemann, U.S. Pat. No. 4,607,520 issued in 1986 to Dam, U.S. Pat. No. 4,651,555 issued in 1987 to Dam and U.S. Pat. No. 5,191,795 issued in 1993 to Fellingham et al.

One major problem presented by using a UABD or other air detector on tubing is that the characteristics of the detection environment change over time during a given procedure and vary from procedure to procedure. For example, the ultrasonic signal output of the transmitting means may vary, the type of tubing may vary and its characteristics may change with time and the sensitivity of the receiving means may vary. In addition, the typical electronic components of a UABD have manufacturing tolerances which can cause variation between otherwise identical UABDs. These variations may not be significant in a chronic care dialysis procedure, because the relatively short duration of the procedure limits their effect. Furthermore, when detecting air in a drip chamber, variations in the detection environment have a less significant effect because a drip chamber air detector is essentially a blood level detector, requiring less sensitivity. The variability may be more important during acute care dialysis because the patient will be connected to the artificial kidney apparatus for an extended period of time when compared with chronic care dialysis, allowing for the accumulation of a greater total effect due to the variations. In some UABDs used in artificial kidney apparatus an automatic gain control (AGC) circuit adjusts the gain of an amplifier stage in the receiving means to maintain a relatively constant average output signal from the amplifier stage in order to compensate for variations in the detection environment.

U.S. Pat. No. 4,015,464 issued in 1977 to Miller et al. illustrates a UABD incorporating an AGC circuit that adjusts the gain of a receiving means amplifier simultaneously adjusting a transmitted signal level and a detected signal level to maintain the circuit in a marginally oscillatory state.

As stated above, the patient undergoing acute care dialysis will be connected to an artificial kidney apparatus system for extended periods of time. Because of this it is not only desirable to prevent infusion of bubbles above a certain size but it is also important that a volume of air infused in a given period of time in the form of bubbles smaller than the discrete bubble size limit, be limited.

In order for the ultrasonic signal to be transmitted through a tube properly the tubing holders used to hold the tube in position desirably positively retain the tube in a position where it is ultrasonically coupled to the tubing holders. Tubing holders such as that proposed in U.S. Pat. No. 4,418,565 issued in 1983 to St. John rely on friction and deformation of a resilient tube to hold the tube in place and do not positively retain the tube. Doors have been used to force the tubing into a tubing holder and to positively retain the tubing in place, but the doors can break off, creating a maintenance task.

It is against this background that the improved UABD of the present invention developed.

SUMMARY OF THE INVENTION

One significant aspect of the present invention is a method and apparatus for detecting inclusions in a liquid flow, such as air bubbles in a blood flow, that compensates for changes in the detection environment without affecting the sensitivity of detection. In accordance with this aspect of the invention, inclusions are detected by transmitting a signal through the fluid and receiving and interpreting the received signal based on the expected degree of attenuation for the liquid and the inclusions. The level or amplitude of the transmitted signal is adjusted to maintain a constant average level of the detected signal, thus compensating for changes in the detection environment. Further in accordance with this aspect of the invention, the average level of the transmitted signal is controlled by integrating the received signal using an integrator with a time constant much longer than the time constant of the expected inclusion signals, and comparing the integrated signal to a constant reference level.

A further significant aspect of the present invention is a method and apparatus for ultrasonic air bubble detection that detects microbubbles and accounts for the total volume of air in the form of microbubbles that is infused into a patient. In accordance with this aspect of the invention the presence of microbubbles is detected and signal comprising a string of high frequency pulses is generated while the microbubbles are present. By counting the pulses, in conjunction with knowledge about the flow of liquid and the anticipated size of the microbubbles, the total amount of air that passes by the detector within a given time period is ascertained.

A still further significant aspect of the present invention is a tubing holder for reliably retaining a flexible tube in an inclusion detector. In accordance with this aspect of the invention, the tubing holder has tubing retention grooves formed into tubing engagement faces, the tubing engagement faces being spaced closer together than the tube diameter. The tube is inserted into the tubing holder by compressing and deforming it against the tubing engagement faces, until it reaches the tubing retaining grooves. Once within the tubing engagement grooves the tube returns to near its original shape and is held in the grooves by its own resilience until it is manually deformed and removed.

A more complete appreciation of the present invention and its advantages can be obtained from understanding the accompanying drawings, which are summarized briefly below, the following detailed description of a presently preferred embodiment of the invention, and the appended claims.

BRIEF DESCRIPTION OF THE DRAWINGS

FIG. 5 is a schematic diagram of an exemplary voltage amplifier circuit incorporated in the improved UABD illustrated in FIG. 2.

FIG. 6 is a schematic diagram of an exemplary demodulator circuit incorporated in the improved UABD illustrated in FIG. 2.

FIG. 7 is a schematic diagram of an exemplary filter circuit incorporated in the improved UABD illustrated in FIG. 2.

FIG. 9 is a schematic diagram of an exemplary test circuit incorporated in the improved UABD illustrated in FIG. 2.

FIG. 10 is a schematic diagram of an exemplary comparator circuit incorporated in the improved UABD illustrated in FIG. 2.

FIG. 11 is a flow chart diagram illustrating the detection of certain component failures in the improved UABD illustrated in FIG. 2

FIG. 12 is a flow chart diagram illustrating the detection of a large bubble and certain component failures in the improved UABD illustrated in FIG. 2

FIG. 13 is a flow chart diagram illustrating the detection of microbubbles in the improved UABD illustrated in FIG. 2

FIG. 14 is a top perspective view of the tubing holder of the present invention with transducer mounting blocks in place.

FIG. 15 is a bottom perspective view of the tubing holder shown in FIG. 14 with transducer mounting blocks removed.

FIG. 16 is an exploded top perspective view of the transducer mounting blocks of the tubing holder shown in FIG. 14 with the housing omitted.

FIG. 17 is a sectional view taken substantially at line 17—17 in FIG. 16.

FIG. 18 is a sectional view taken substantially at line 18—18 in FIG. 14 illustrating the tube partially inserted into the tubing holder.

FIG. 19 is the sectional view of FIG. 18 illustrating the tube inserted into and retained by the tubing holder.

DETAILED DESCRIPTION

Figure 1:
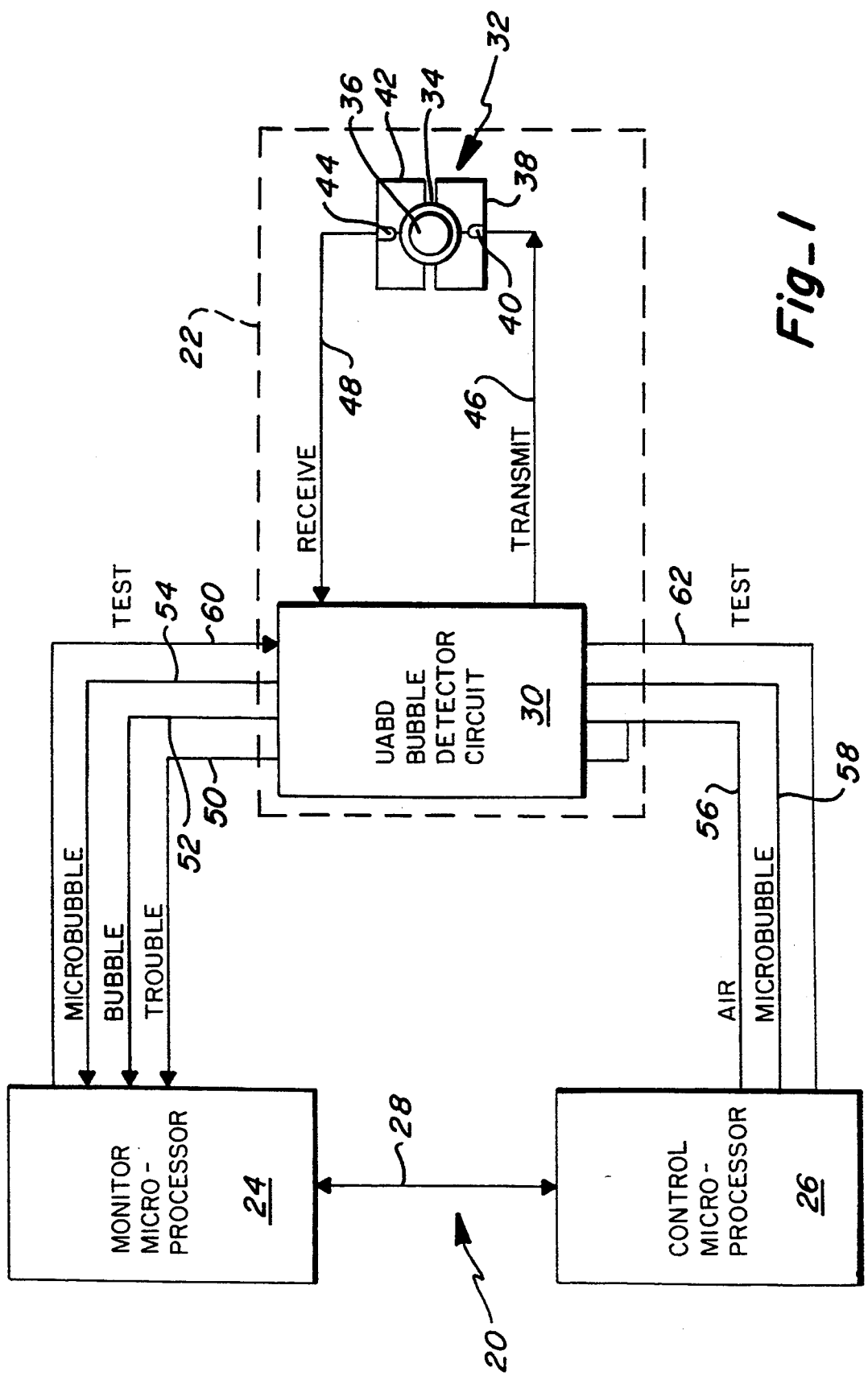
FIG. 1 is a block diagram of an acute care artificial kidney apparatus incorporating the improved ultrasonic air bubble detector (UABD) of the present invention.

A preferred embodiment of the ultrasonic air bubble detector (UABD) of the present invention will be described by reference to FIGS. 1-20. Like reference numerals in different figures denote like parts.

Although described by reference to a UABD it will be appreciated by those having skill in the art that aspects of the present invention may be applied to the detection of other inclusions in liquids, such as the detection of solid inclusions. It will be further appreciated by those having skill in the art that the invention is applicable to other signal types, such as infrared, visible and ultraviolet light, radiation or radio frequency energy, which are differently attenuated by a liquid and the inclusions to be detected.

Referring to FIG. 1, an acute care artificial kidney apparatus 20 includes the UABD 22 of the present invention and two microprocessors 24, 26 for monitoring and controlling the acute care artificial kidney apparatus 20. The monitor microprocessor 24 and the control microprocessor 26 are complementary units which communicate 28 with each other to compare various operating parameters of the artificial kidney apparatus 20, thus guarding against a single point component failure causing patient injury. The UABD 22 incorporates a bubble detector circuit 30 and a tubing holder 32 for transmitting and receiving an ultrasonic signal through a tube 34 through which blood 36 is flowing. The tube 34 is typically flexible plastic tubing that is part of a disposable tubing kit used in a blood processing system. The tubing holder 32 comprises a first or transmitter mounting block 38 into which a piezoelectric ultrasonic transmitting transducer 40 is mounted and a second or receiver mounting block 42 into which a piezoelectric ultrasonic receiving transducer 44 is mounted. The piezoelectric transducers 40,44 provide an efficient method for electrical to ultrasonic and ultrasonic to electrical energy conversion. Ultrasound emitted by the transmitting transducer 40 is sent through the tube 34 and blood 36 and is detected by the receiving transducer 44. The tube is held between the two transducers 40, 44 by the mounting blocks 38, 42 of the tubing holder 32. A slight curved or arcuate surface in each mounting block 38, 42 holds the tube 34 in place and provides the necessary contact area to enhance sound coupling into the fluid filled tube with a minimum of deformation of the tube. The bubble detector circuit 30 generates an electrical drive signal 46 which drives the transmitting transducer 40. The transmitting transducer 40 vibrates mechanically in response to the drive signal 46 causing an ultrasonic signal to pass through the tube 34 and blood 36. The ultrasonic signal causes the receiving transducer 44 to vibrate mechanically producing an electrical received signal 48. When an air bubble passes through the detection area, some of the sound is absorbed and causes a reduction or attenuation of level of sound detected by the receiving transducer 44. The received signal 48 is related to the bubble size. The bubble detector circuit 30 receives the received signal 48 from the receiving transducer 44 in inverse proportion to the air in the blood 36.

The bubbles cause reductions in the received signal 48 that range from about 5%, for very small bubbles, to almost 100% for much larger bubbles. Bubbles larger than about 8 microliters ($\mu L$) in volume (2.5 millimeters (mm) in diameter) block a substantial portion of the signal from reaching the receiving transducer 44. Small bubbles of about 1 $\mu L$ in volume (0.58 mm diameter) produce ultrasound signals that correspond to about 12% of the normal quiescent ultrasonic signal. When no tube 34 is in place, or when the tube 34 is not filled with fluid 36, virtually no ultrasonic signal is received.

The received signal 48 is interpreted by the bubble detector circuit 30 to create a plurality of output signals 50, 52, 54, 56, 58 which are then transmitted to the monitor microprocessor 24 and control microprocessor 26. In addition to the signals sent to the microprocessors 24, 26, the microprocessors can each generate a test initiation signal 60, 62 which simulates the occurrence of a bubble and verifies that the bubble detector circuit 30 is functioning properly. During initial system turn-on or at any other time, the entire bubble detector circuit 30 can be tested. Both large and small bubble conditions can be simulated from commands sent by both of the microprocessors 24, 26. The commands produce signals that emulate those produced by actual bubbles. Problems in the circuit may then be detected during the test.

Figure 2:
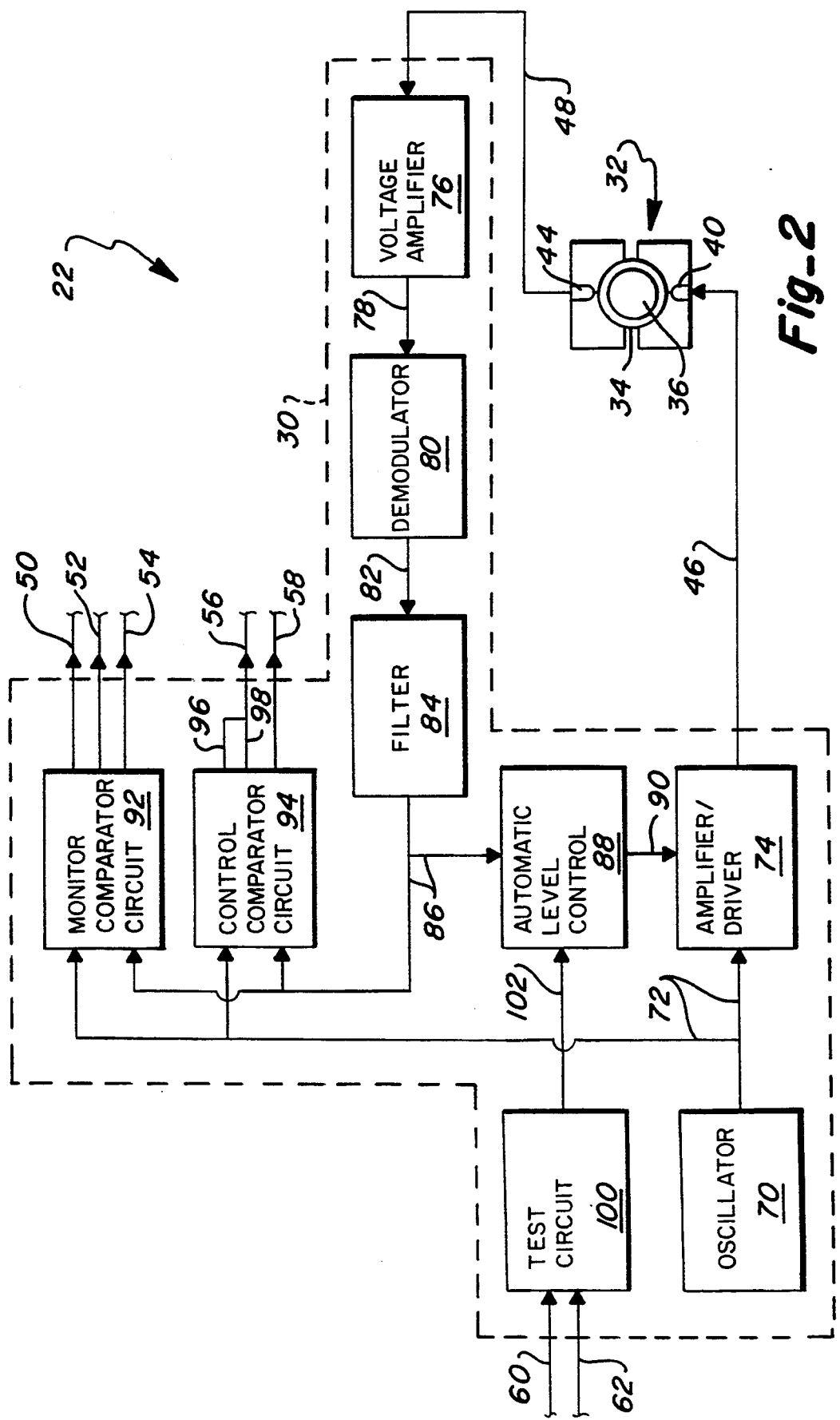
FIG. 2 is a block diagram of the improved UABD of the present invention illustrated in FIG. 1.

The functions of the bubble detector circuit 30 are described generally by reference to FIG. 2. The bubble detector circuit includes an oscillator circuit 70 which generates a 2.45 megahertz (MHz) timing signal 72 at relatively low power levels. The timing signal 72 is amplified by an amplifier/driver circuit 74 which produces the necessary 2.45 MHz, relatively high power level, drive signal 46 necessary to drive the transmitting transducer 40 of the tubing holder 32. The ultrasonic sound transmitted through the tube 34 and blood 36 is received by the receiving transducer 44. The received signal 48 is conducted to a voltage amplifier circuit 76 which amplifies the received signal and conducts an amplified signal 78 to a demodulator circuit 80. The demodulator circuit 80 produces a DC rectified signal 82 proportional to the amplified signal 78 which is in turn filtered by a filter circuit 84 to produce a filtered signal 86 having a constant average voltage level, preferably approximately 2.5 volts.

The average filtered signal 86 level is controlled by an automatic level control (ALC) circuit 88 which produces a control signal 90 that adjusts the drive signal 46 from the amplifier/driver circuit 74 to maintain the average level of the filtered signal 86 at approximately the desired constant voltage level. The ALC circuit 88 compensates for variations in the detection environment such as transmitting transducer sound output variation, tube 34 material changes, receiving transducer 44 sensitivity variations and component tolerances. The ALC circuit 88 thus tends to assure that the UABD always reacts the same to particular bubble sizes.

The filtered signal 86 from the filter circuit 84 is split and fed into two similar voltage comparator circuits 92, 94. A monitor comparator circuit 92 produces the output signals 50, 52, 54 for use by the monitor microprocessor 24 (FIG. 1) and the control comparator circuit 94 produces output signals 56, 58 for use by the control microprocessor 26 (FIG. 1). The redundant comparator circuits 92, 94 facilitate safe operation of the UABD 22 and the artificial kidney apparatus 20 (FIG. 1) in the event of a component failure.

Each comparator circuit 92, 94 delivers three separate logic signals. A trouble signal 50, 96 corresponds to certain failures in the detector circuit 30, and will change state whenever the ultrasound signal goes above an acceptable limit 32. A bubble signal 52, 98 produces a logic output whenever a large, 10 $\mu L$ or greater, bubble is detected or when there is no tube 34 installed in the tubing holder. A microbubble signal 54, 58 produces a logic swing whenever a small, 1.0 $\mu L$ or greater, is detected. The microprocessors 24, 26 count the number of microbubble events through a fixed time frame, e.g., one minute, and shut down the artificial kidney apparatus 20 (FIG. 1) if a predetermined number of events per unit time is exceeded. The trouble signal 96 and the bubble signal 98 from the control comparator circuit 94 are tied together to form a single air signal 56.

During artificial kidney apparatus 20 (FIG. 1) operation, the microprocessors 24, 26 (FIG. 1) periodically monitor the bubble counts. If a sufficient number of microbubble clock pulses are detected for the artificial kidney apparatus's 20 specific fluid pumping rate, one of the microprocessors 24, 26 will activate an alarm and shut down the artificial kidney apparatus 20. Likewise, if one of the microprocessors 24, 26 (FIG. 1) receives a large bubble signal 52, 98 or a trouble signal 50, 96 it will activate an alarm and command the artificial kidney apparatus 20 to stop.

A test circuit 100 is provided to generate a simulation signal 102 to simulate the presence of a bubble or a series of microbubbles upon command from the monitor microprocessor 24 or the control microprocessor 26 by interfacing with the ALC circuit 88.

Figure 3:
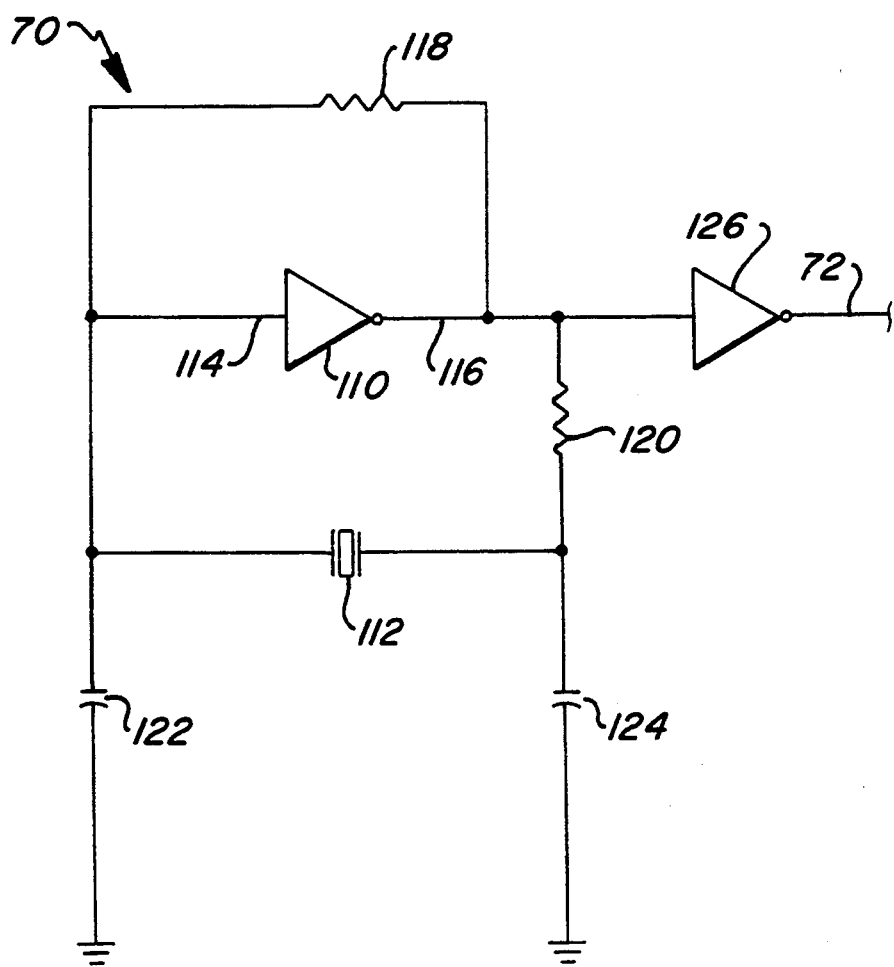
FIG. 3 is a schematic diagram of an exemplary oscillator circuit incorporated in the improved UABD illustrated in FIG. 2.

To produce the necessary ultrasonic signal, the piezoelectric sound emitting transmitting transducer 40 is driven by a constant frequency, variable amplitude driver signal 46 produced by the oscillator circuit 70 and amplifier driver circuit 74 as will be described by reference to FIGS. 3 and 4. The oscillator circuit 70, illustrated in FIG. 3, comprises by a quartz crystal oscillator. The oscillator comprises a high speed unbuffered C-MOS inverter, preferably one section of a 74HCU04 integrated circuit (IC). The unbuffered inverter is used to promote linear operation of the oscillator circuit 70. An "AT" cut quartz crystal 112 that is designed for parallel resonant operation is connected to the inverter input 114.

The oscillator circuit 70 is a variation of the conventional "Pierce" oscillator. A resistor 118, preferably 1 megaOhms (MΩ) connected from the output 116 to the input 114 of the inverter 110 biases the inverter into the linear one half supply point. A suppression resistor 120 preferably 2.12 kiloOhms (kΩ) connected between the output 116 and the crystal 112 suppresses spurious high frequency oscillations and isolates the output from the crystal 112. With the suppression resistor 120 installed, the inverter output 116 has a square wave form signal. The suppression resistor 120 is picked to be roughly the reactance of the quartz crystal 112 at its resonant frequency. The signal from the input 114 to the output 116 of the inverter is phase shifted 180 degrees by the logic inversion. The quartz crystal 112 appears as a large inductance, since it is operated in the parallel resonance mode. The addition of a capacitor 122 at the input and a capacitor 124, each preferably about 22 picoFarads (pF) at the output of the inverter circuit produce a pi network. Such a network provides an additional 180 degree phase shift to sustain oscillation. The load capacitance is usually specified by the quartz crystal manufacturer.

Since the open loop gain of the inverter 110 is about ten, there is sufficient gain to overcome the circuit losses to insure stable oscillation. The output signal is then buffered by a second C-MOS logic inverter 126, preferably contained within the same 74HCU04 IC package, to produce the timing signal 72. During operation, the timing signal 72 output of the oscillator 70 is a 5 volt peak-to-peak square wave signal.

Figure 4:
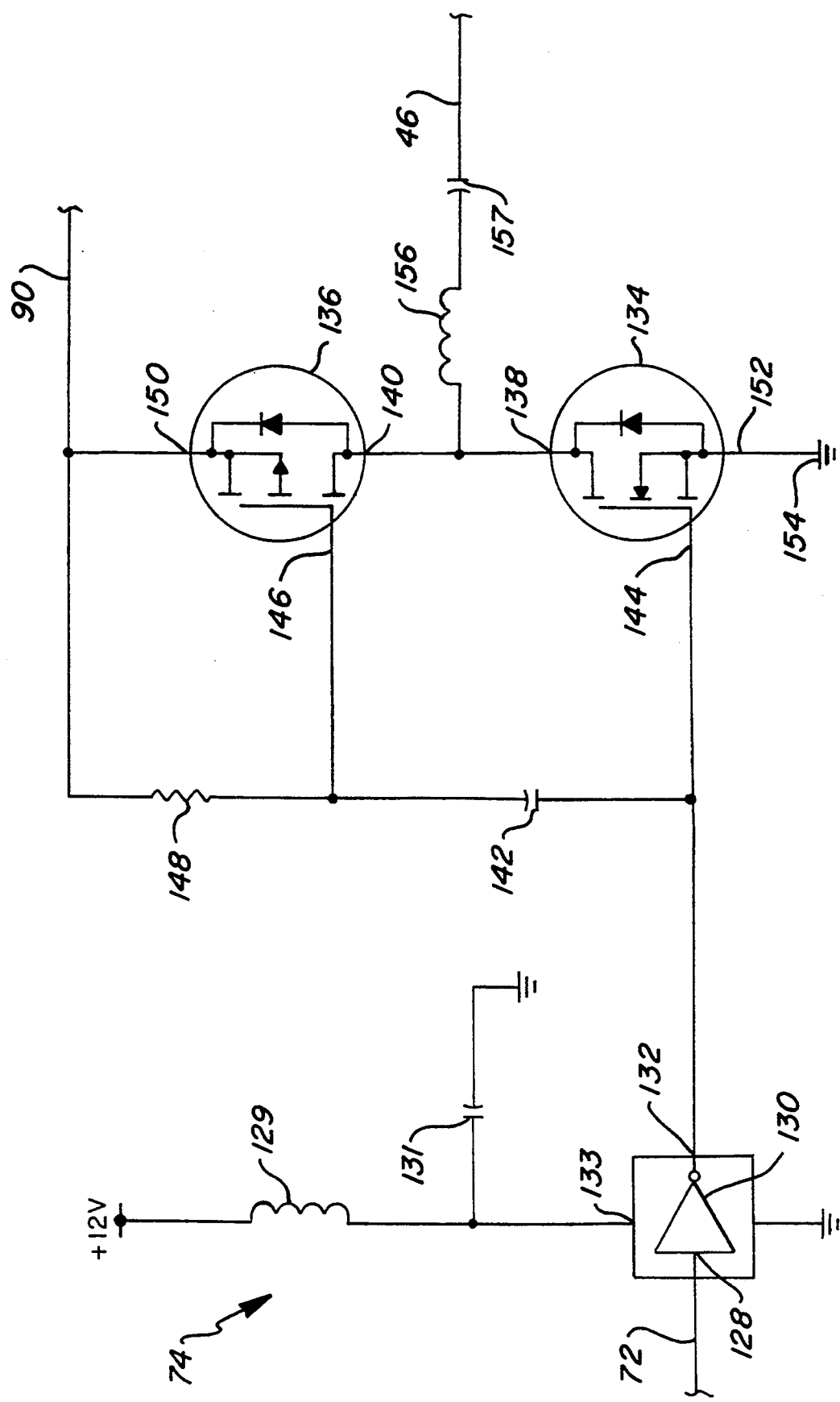
FIG. 4 is a schematic diagram of an exemplary amplifier/driver circuit incorporated in the improved UABD illustrated in FIG. 2.

The operation of the power amplifier/driver circuit 74 is illustrated in FIG. 4. The 5 volt peak-to-peak square wave timing signal 72 that emerges from the oscillator circuit 70 (FIG. 2) is fed to the input 128 of an inverting power driver 130, preferably an ICL7667 IC. The power driver 130 converts the 5 volt peak to peak signal into a 12 volt peak-to-peak square wave output signal. The power driver 130 is specifically selected to drive power field effect transistors (FETs). Since power FETs are noted for their high input capacitance, the ICL7667 has been specifically designed to supply a load with high peak currents. The ICL7667 can drive loads with peak currents up to 1.5 amps. The high drive current allows an FET device to be turned on and off in less than 50 nanoseconds. An inductor 129, preferably 470 microHenries (μH), and a capacitor 131, preferably 0.1 microFarads (μF), are connected to the power pin 133 of the power driver 130. The inductor 129 and capacitor 131 are connected as a conventional L-section low pass filter to block the high frequency timing signal 72, preventing it from entering the +12 volt power supply.

The output 132 of the power driver 130 is fed to a complementary power FET circuit, which consists of one N-channel FET 134, preferably ZVN2106A, and one P-channel FET 136, preferably ZVP2106A. The drain terminals 138, 140 of the two FETs 134, 136 are connected together. The N-channel FET 134 is turned on during the low-to-high transition of the power driver's 130 output signal, while the P-channel FET 136 is turned on during the high-to-low transition. A capacitor 142, preferably 0.1 μF connected between the gates 144, 146 of the FETs 134, 136 couples the output of the power driver 130 to the P-channel FET 136. A resistor 148, preferably 1 kΩ connected between the gate 146 and source 150 of the P-channel FET 136 is used to bias the P-channel FET 136 into the off state. Each FET 134, 136 requires a minimum voltage threshold of about 3 volts between the gate and source to begin turning on. Therefore the 12 volt voltage swing from the power driver 130 insures each FET 134, 136 will be turned on hard, keeping the drain-to-source resistance low.

The variable voltage ALC signal 90 is connected to the source of the P-channel FET 136. The source of the n-channel FET 134 is connected to circuit ground 154. When turned on fully, the P-channel FET 136 provides a low resistance path from the ALC signal 90 supply voltage to the output. Conversely, when turned on, the N-channel FET 134 provides a low resistance path from the output to circuit ground 154. The two FET 134, 136 combination generates a square wave output signal that swings from the voltage level of the ALC signal 90 to ground with low loss. Since the upper P-channel FET source voltage is controlled by the ALC signal 90 from the ALC circuit 88, the transmitting transducer 40 (FIG. 2) peak-to-peak drive signal 46 can be varied over a wide range. The upper drive voltage is restricted by power dissipation of the transmitting transducer 40 (FIG. 2). However, the lower voltage level can, in theory, be as low as a few millivolts.

With the two drain terminals 138, 140 of the two FETs 134, 136 connected together, the output signal has a square wave form, with fast rise and fall times. Since the transmitting transducer 40 (FIG. 2) has a high capacitance, up to 1000 pF, an inductor 156 preferably 5.6 μH, and a capacitor 157, preferably 0.1 μF are placed between the FETs 134, 136 and the transducer 40 (FIG. 2). The capacitor 157 isolates the transmitting transducer 40 from any DC voltage delivered by the amplifier/driver circuit 74. The inductor 156 limits the peak currents that would otherwise flow through the transducer 40 if a direct connection were made. In addition, the voltage rise and fall times are also limited by the inductor 156. The inductor 156 thereby reduces the broadband radio signals that would otherwise be emitted, if a direct connection were made to the FETs 134, 136. With the inductor 156 in place the drive signal 46 that is produced across the transducer 40 (FIG. 2) resembles a pure sine wave with minimum harmonics. In addition, the peak-to-peak voltage produced by the inductor 156 across the transducer 40 (FIG. 2), is slightly greater than the peak-to-peak drive voltage. With an 11 volt peak-to-peak output from the two FETs 134, 136 the voltage seen across the transmitting transducer can exceed 15 volts peak-to-peak. At 15 volts peak-to-peak, the power dissipation at the transmitting transducer 40 (FIG. 2) is less than 0.25 watts. Further, the inductor 156 limits the current that can be delivered by the amplifier/driver circuit 74 thus providing short circuit protection. With the inductor 156 in place the drive signal 46 can be continuously shorted to ground with no ill effects on the bubble detector circuit 30.

The ultrasound signal voltage amplifier circuit 76 will be described in conjunction with FIG. 5. The ultrasound voltage received signal 48, produced by the piezoelectric receiver transducer 44 (FIG. 2), is amplified using a high frequency operational amplifier 160. The high frequency amplifier is preferably an AD829 operational amplifier IC chosen for its wide bandwidth, linearity and stability. An amplifier gain of 40 is needed to boost the weak received signal 48 to produce an amplified signal 78 having an amplitude of 3 volts peak-to-peak. At 3 volts the raw ultrasound signal can be efficiently demodulated to extract the sometimes small bubble signals. To obtain a gain of 40 at the 2.45 MHz ultrasound frequency, the amplifier's 160 unity gain bandwidth has to be greater than about 80 MHz. The AD829 operational amplifier IC has a unity gain bandwidth of 120 MHz.

The amplifier 160 IC is connected as a modified non-inverting amplifier circuit. A blocking capacitor 161, preferably 0.01 $\mu$F, interconnects the received signal 48 and a non-inverting input 162 of the amplifier 160. The blocking capacitor 161 AC couples the non-inverting input 162 to the received signal, blocking any DC component of the received signal 48 and attenuating any stray low frequency components of the received frequency, such as 60 Hertz (Hz) hum, while passing the desired high frequency component of the received signal 48 without significant attenuation. In the non-inverting configuration, the received signal 48 is fed directly to the non-inverting input 162 of the amplifier 160, while the amplifier's 160 inverting input 164 is supplied with a signal that is generated by feeding back a small amount of the amplifier's output 166. In the conventional non-inverting circuit, a two resistor 168, 170 voltage divider would determine the amount of signal fed back to the inverting input 164 and would therefore determine the voltage gain of the amplifier circuit 76. A first resistor 168, preferably 4.32 k$\Omega$, is connected between the amplifier 160 output 166 and the inverting input 164 and a second resistor 170, preferably 100 Ohms ($\Omega$) is connected between the inverting input and circuit ground 154. However, the conventional non-inverting circuit has been modified so the amplifier has a high gain for the high frequency ultrasound signal and a gain of only one for DC. A capacitor 172, preferably 0.01 $\mu$F, in series with the second resistor 170, interposed between the resistor 170, and circuit ground 154 provides the needed DC isolation. The modified non-inverting circuit allows the amplifier's gain to be controlled by a single resistor, without disturbing the DC bias point. The capacitor 172 insures that the amplifier preferentially amplifies only high frequency signals. Two resistors 174, 176, each preferably 4.32 k$\Omega$, are connected to the non-inverting input 162 to form a second voltage divider network that biases the amplifier 160 to about the half way point between the +12 volt and the −5 volt supplies, approximately +3.5 volts. The biasing maximizes the amplifier's peak-to-peak output voltage swing and moves the normal operating point away from −5 volt power supply.

With the values chosen, the amplifier's gain is set at about 40. To insure stable operation, a phase compensation capacitor 178, preferably 10 pF, is added and is connected to the amplifier's 160 compensation pin 180. The capacitor 178 value is chosen to keep the circuit 76 free of spurious oscillations, without reducing the overall gain.

The signal demodulator circuit 80 will be described by reference to FIG. 6. The demodulator circuit 80 comprises a conventional half wave voltage doubling rectifier circuit operative on the amplified signal 78. The demodulator circuit 80 converts the amplitude modulated 2.45 MHz amplified signal 78, that emerges from the amplifier circuit 76 (FIG. 2), into the DC voltage rectified signal 82. The demodulator 80 circuit comprises a first diode 186, a second diode 188, a first capacitor 190, a second capacitor 192 and a resistor 194 connected in a well known configuration to form the half wave voltage doubling rectifier circuit. The first and second capacitors 190, 192 are each preferably 0.01 $\mu$F and the resistor 194 is preferably 10 k$\Omega$. During operation, the DC voltage level of the rectified signal 82 will fluctuate downward whenever an air bubble passes between the ultrasound transducers. To increase the rectification efficiency, the diodes 186, 188 are preferably Schottky diodes, 1N5818. Schottky diodes have a lower voltage drop (about 0.25 volts) than the more conventional signal diodes (about 0.6 volts) and when used in the voltage doubler circuit will produce a DC voltage rectified signal 82 of about 2.5 volts from a 2.8 volt peak-to-peak amplified signal 78.

The capacitor 192 and resistor 194 form a conventional low pass filter network. The values of the capacitor 192 are selected to filter out most of the 2.45 MHz carrier without attenuating signals associated with bubbles.

The filter circuit 84 will be described by reference to FIG. 7. To remove the 2.45 MHz carrier signal that may remain, a conventional second order Butterworth low pass active filter 84 is used after the demodulator circuit 80. The active Butterworth type low pass filter 84 is made using a low frequency operational amplifier 204, preferably an LF411 IC. Although the filter circuit 84 does not provide any additional gain, it does buffer the signal so it can be routed to many other active circuits without being attenuated. The 3 decibel (db) frequency knee of the Butterworth filter is set at about 1 kilohertz. Such a frequency is based on the highest expected frequency of interest, associated with bubbles passing through the detector at the maximum flow rate of 180 milliliters (mL) per minute. The second order Butterworth filter attenuates signals higher than 1 kHz with a 12 db per octave slope.

The ALC circuit 88 maintains a constant average signal level, as seen at the filtered signal 86 output of the filter circuit 84 as will be described in conjunction with FIG. 8. Because the voltage input to the comparator circuits 92, 94 (FIG. 2) is held to a constant average value by the ALC circuit 88 the sensitivity of detection will remain constant. The ALC circuit 88 controls the voltage fed to the transducer amplifier/driver circuit 74 so the filtered signal 86 is maintained at a constant average signal level. Factors in the bubble sensing environment that may influence the average signal level can therefore be compensated for. With the components selected, the filtered signal 86 output from the filter circuit 84 should always average very close to 2.5 volts. The ALC circuit 88 consists of an inverting integrator 206 and an ALC voltage amplifier 208. The conventional inverting integrator 206 comprises an operational amplifier 210, preferably an LF412A IC, that compares the filtered signal 86 output voltage from the filter circuit 84 (FIG. 2) with a DC reference voltage 214. A feedback capacitor 212, preferably 1.0 μF, is connected between an output 207 of the operational amplifier 210 and an inverting input 209 of the operational amplifier 210. The DC reference voltage 214 is generated by voltage divider network made up of two resistors 216, 218, each preferably 10 kΩ and a capacitor 220, preferably 0.01 μF and is connected to a non-inverting input 211 of the operational amplifier. To insure stability and accuracy, the voltage used by the divider network is derived from a first precision voltage reference source 222. The first voltage reference source 222 is generated by a precision voltage source IC (not shown), preferably a REF-02 IC, which provides a very precise 5 volt output. The integrator's 206 output signal 224 slowly adjusts upward if the received average filtered signal 86 voltage level is less than the reference voltage 214 and adjusts downward if the filtered signal 86 is greater than the reference voltage 214. The effect is a conventional negative feedback control circuit that has integral action and a slow response time.

The integrator circuit 206 permits a high gain to insure control accuracy but has an intentionally slow response time. The slow response allows the sudden level changes associated with bubbles to be ignored by the ALC circuit 88. The response time is selected to be slower than the signals of interest caused by bubbles by about ten times in the preferred embodiment.

The filtered signal 86 is connected to the inverting input 209 of the operational amplifier 210 through a first response time determining resistor 213 and a second response time determining resistor 215. The first resistor 213 is connected in series between the filtered signal 86 and the inverting input 209. For low level signals, such as those produced by small bubbles, the first response time determining resistor 213, preferably 1 MΩ, and the feedback capacitor 212, preferably 1.0 μF, establish a relatively slow one second response time. The second response time determining resistor 215, preferably 100 kΩ, is connected in series with a diode 217, preferably 1N4148, and the series combination is connected in parallel with the first resistor 213. The second resistor 215 is activated only during large changes in the filtered signal 86, such as from a large bubble, to produce a relatively faster 0.1 second response time. A slow positive response time is needed to ignore sudden changes in the filtered signal 86 level due to bubbles. Following the detection of bubbles, a faster negative response time is allowed to restore the initial level of the filtered signal 86. The asymmetrical reaction of the integrator 86 to signal changes minimizes distortion of bubble signal amplitudes and minimizes over correction voltages. The faster response time to large signal changes is especially useful when the artificial kidney apparatus 20 (FIG. 1) is initially turned on and when the tube 34 (FIG. 1) is installed in the tubing holder 32 (FIG. 1). Under these conditions the ALC circuit 88 quickly reestablishes normal UABD operation.

The output 224 of the integrator 206 is fed to the ALC voltage amplifier 208. The ALC voltage amplifier 208 comprises a conventional non-inverting operational amplifier 226, preferably a part of the same LF412A IC package as the integrator operational amplifier 210. The output of the operational amplifier 226 is connected to the base 228 of an NPN Darlington transistor 230, preferably 2N6725, through a Zener diode 232, preferably 1N4728A. The Darlington transistor 230 forms a transistor buffer circuit which allows more current to be controlled than would be possible using the operational amplifier 226 alone. A feedback resistor 229, preferably 10 kΩ, connected between the emitter 231 of the Darlington transistor 230 and the inverting input 233 of the operational amplifier 226 and an additional resistor 235, preferably 10 kΩ, connected between the inverting input of the operational amplifier 226 and circuit ground 154 determine the gain of the ALC voltage amplifier 208. The Zener diode 232 provides a voltage level shift. The level shift is needed to compensate for the inability of the operational amplifier 226 to swing to both the plus and minus supply voltages. Typically, with a +12 volt and a −5 volt supply the operational amplifier 226 will only be able to swing from +10 volts to −3 volts. With the Zener diode 232 in place, the base 228 of the Darlington transistor 230 can be fed with a voltage that swings from 0 volts to 12 volts. Of course, since the Darlington transistor has a finite voltage drop of about 1 volt, the actual voltage swing fed to the transducer amplifier/driver circuit 74 (FIG. 2) is from 0 volts to about 11 volts. A buffer capacitor 237, preferably 4.7 μF connected between the emitter 231 of the Darlington transistor 230 and circuit ground 154 provides a low source impedance to the amplifier/driver circuit 74 (FIG. 2). An inductor 239, preferably 470 μH, and a capacitor 241, preferably 0.1 μF, form a conventional L-section low pass filter between the emitter 231 of the Darlington transistor 230 and the ALC signal 90. The inductor 239 and capacitor 241 prevents the high frequency 2.45 MHz signals from interfering with the ALC circuit 88. With the ultrasonic amplifier gain set at 40 and a wide ultrasonic drive voltage swing, the ALC circuit 88 has a compensation range of over 30 db (30:1).

Figure 8:
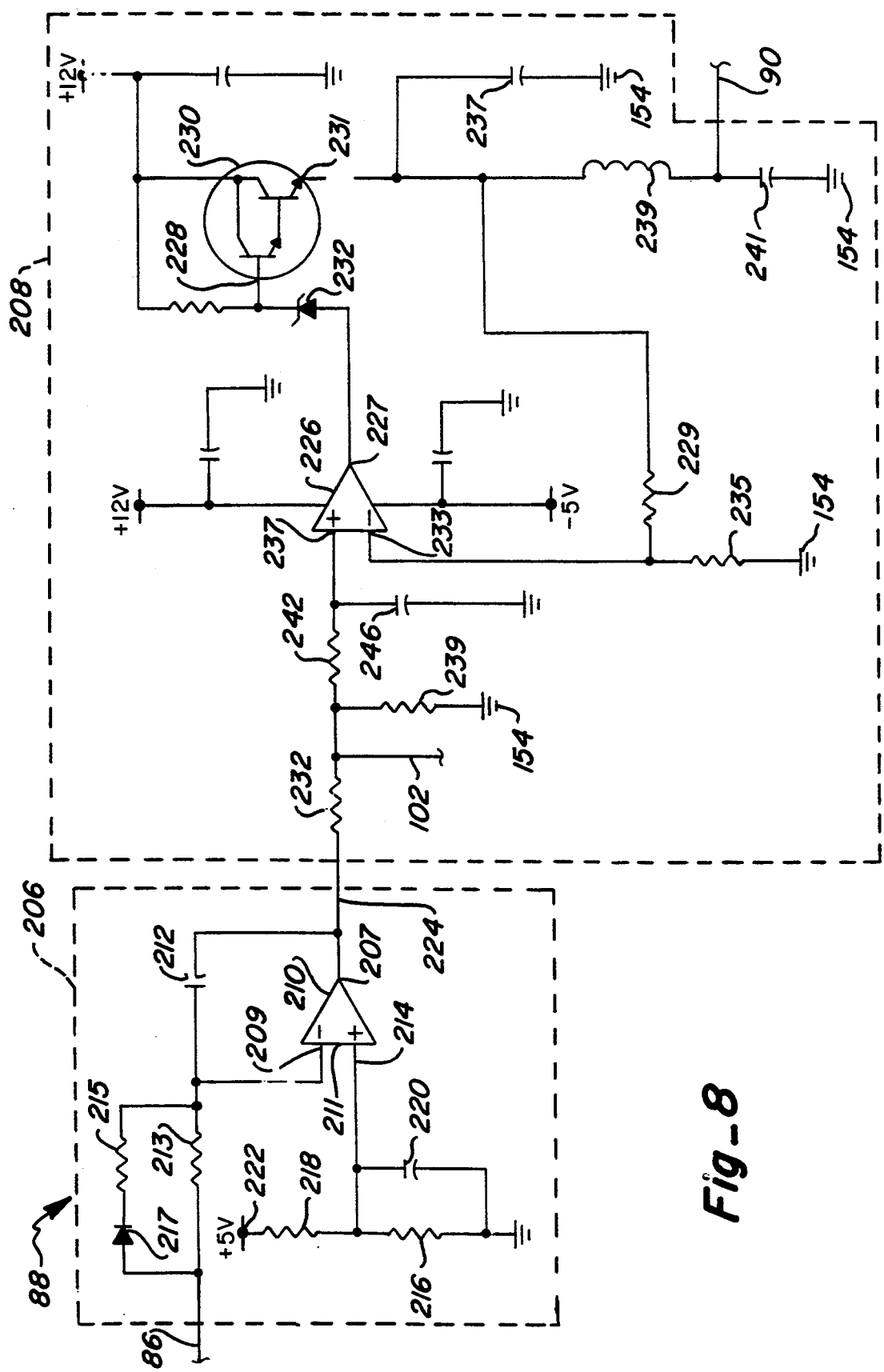
FIG. 8 is a schematic diagram of an exemplary automatic level control circuit incorporated in the improved UABD illustrated in FIG. 2.

Referring to FIGS. 8 and 9, the test circuit 100 interacts with the ALC circuit 88 to permit generating sudden level changes in the ultrasonic signal transmitted by the transmitting transducer 40 (FIG. 2) to simulate various sizes of bubbles for testing purposes. The sudden level changes are detected by the voltage amplifier circuit 76 (FIG. 2), the demodulator circuit 80 (FIG. 2), the filter circuit 84 (FIG. 2) and the comparator circuits 92, 94 (FIG. 2) as bubble signals. The simulated signals can be used during artificial kidney apparatus 20 (FIG. 1) testing and will test the operation of the bubble detector circuit 30 (FIG. 2). To allow the test signals to be injected into the detector circuit 30, the output of the integrator circuit is first attenuated by factor of two by a first attenuation resistor 232, preferably 10 kΩ, connected in series between the output 224 of the integrator 206 and the non-inverting input 237 of the operational amplifier 226 of the ALC voltage amplifier 208. A second attenuation resistor 239, preferably 20 kΩ, is connected between circuit ground 154 and the non-inverting input 237 of the operational amplifier 226. The signal loss is compensated for by setting the voltage amplifier's 226 gain at two by selection of the gain determining resistors 229, 235.

Under normal operation the output of the voltage amplifier 226 is identical to the output of the integrator 224. However, a third attenuation resistor 234, preferably 15.8 kΩ, is included in the circuit and can be switched into the circuit using a monitor test FET 238, preferably 2N7000, that connects the resistor 234 between the non-inverting input 237 of the operational amplifier 226 of the ALC voltage amplifier 208. Further, a fourth attenuation resistor 236, preferably 3.92 kΩ, is included in the circuit and can be switched into the circuit using a control test FET 240, preferably 2N7000, that connects the resistor 236 between the non-inverting input 237 of the operational amplifier 226 of the ALC voltage amplifier 208. When activated by a logic level test signal 60, 62 swing, the FET switches change the ratio of the attenuation network and thus the output voltage of the amplifier 226. When switched into the circuit, the resistors 234, 236 decrease the amplifier's 226 output voltage by a fixed ratio, thus lowering the voltage levels of the ALC signal 90 and the transducer drive signal 46 (FIG. 2) by the same proportion, regardless of the actual voltage used to maintain an average received ultrasound level. During testing a small 1 μL microbubble can be simulated by energizing the monitor test signal 60, thereby turning on the monitor test FET 238 causing a sudden 24% drop in the normal drive voltage, which forces the received signal 48 (FIG. 2) to also drop by 24%. Likewise, a 10 μL bubble can be simulated by activating control test signal 62, thereby turning on the control test FET 240 dropping the drive voltage by 56%. Since the voltage change, during activation of either of the two FETs 238, 240 occurs after the slow responding integrator, the sudden drive voltage drop will produce a signal similar to a signal produced by a bubble.

To insure the signal level changes are not too fast, a resistor 242, preferably 20 kΩ, and capacitor 246, preferably 0.047 μF, connected as a conventional L-section low pass filter network is installed between the attenuation resistors 232, 234, 236, 239 and the non-inverting input 237 of the operational amplifier 226 at the input of the voltage amplifier 226. The network slows down the level change and makes the signals produced at the ultrasound receiver appear more like actual bubble signals, that normally have finite rise and fall times. In the preferred embodiment the two components used result in a time constant is about 2.3 ms.

The voltage comparator circuits 92, 94 (FIG. 2) will be described by reference to FIG. 10. FIG. 10 illustrates the monitor comparator circuit 92. The control comparator circuit 94 (FIG. 2) is substantially identical to the monitor comparator circuit 92 except for those differences specifically described below.

To promote machine safety, two separate comparator circuits 92, 94 (FIG. 2) are used. The monitor comparator circuit 92 feeds signals 50, 52, 54 to the monitor processor 24 (FIG. 1) while the control comparator circuit 94 (FIG. 2) feeds signals 56, 58 (FIG. 1) to the control processor 26 (FIG. 1). Should a component failure occur in one comparator circuit 92, 94 (FIG. 2), the other circuit would still be able to operate correctly. However, since both comparator circuits 92, 94 (FIG. 2) should operate in a similar fashion, disagreement between the two circuits may be detected by the communication 28 (FIG. 2) between the two microprocessors 24, 26 (FIG. 1) and could force an alarm or shutdown of the artificial kidney apparatus 20 (FIG. 1).

Each voltage comparator circuit comprises three comparators 250, 252, 254. Each comparator is a voltage comparator, preferably an LM339A IC, which compares the filtered signal 86 with a reference voltage derived from the precision voltage source 222. The control comparator circuit 94 has a separate associated second precision voltage source IC (not shown), so that a failure of a precision voltage source IC will cause a disagreement between the microprocessors 24, 26 (FIG. 1) as described above.

A first comparator 250 of the comparator circuit 92 detects component failures in the bubble detector circuit 30 (FIG. 2). A second comparator 252 detects the presence of relatively large bubbles in the tube 34. The third comparator 254 detects the presence of microbubbles in the tube. The presence of each microbubble is transmitted to the corresponding microprocessor so that the microprocessor can count the bubbles and determine the number encountered within a discrete period of time.

A pull-up resistor 256, 258, 260 preferably 2.21 kΩ connects each comparator 250, 252, 254 output 262, 264, 266 to +5 volt power supply VCC to provide a standard transistor-transistor logic output swing of 5-to-0 and 0-to-5 volts.

The filtered signal 86 is connected to the inverting input 268 of the first comparator 250 through an isolation resistor 270. The 5 volt precision supply 222 is connected to the non-inverting input 272 of the first comparator through voltage divider network made up of two resistors 274, 278, selected so that the reference voltage at the non-inverting input of the first comparator is 2.8 volts. A feedback resistor 276, preferably 442 kΩ, interconnects the non-inverting input 272 and the output to provide positive feedback. The positive feedback induces hysteresis and causes the output logic level shift to be definite and without oscillations. The comparator output 262 is connected as the trouble signal 50 to the microprocessor 24 (FIG. 1). In the case of the control comparator circuit 94 the first comparator non-inverting input is tied to the second precision voltage source through a pull-up resistor only, preferably 10 kΩ, so that the reference voltage is 5 volts.

The filtered signal 86 is connected to the non-inverting input 278 of the second comparator 252 through an isolation resistor 280. The 5 volt precision supply 222 is connected to the non-inverting input 282 through a voltage divider network made up of two resistors 284, 286 selected so that the reference voltage at the non-inverting input 282 of the second comparator 252 is 1.2 volts. A feedback resistor 288, preferably 1 MΩ, connected between the non-inverting input 278 and the output 264 provides positive feedback. The comparator output 264 is connected as the bubble signal 52 to the microprocessor 24 (FIG. 1) through a D flip-flop latch 265, preferably 74HC74 IC, associated with the microprocessor 24. The D flip-flop latch 265 output 267 communicates the occurrence of a bubble to the microprocessor 24 and the microprocessor 24 is connected to reset 267' D flip-flop latch 265.

The third comparator's 254 inverting input 290 is connected to the filtered signal 86 through an isolation resistor 292. The non-inverting input is connected to the 5 volt precision supply 222 through a voltage divider network made up of two resistors 296, 298 selected so that the reference voltage at the non-inverting input is 2.2 volts. A feedback resistor 300, preferably 1 MΩ, connected between the output 266 and non-inverting input 294 provides positive feedback. The output 266 of the third comparator 254 is connected to the input 302 of a standard J-K flip-flop, preferably a 74HC76 IC. The K input 306, inverting clear input 308, and inverting preset inputs 310 are all held at a logical high state by virtue of being connected to the +5 volt logic power supply VCC. The clock input 312 is connected to the 2.45 MHz timing signal 72 from the oscillator circuit 70 (FIG. 2). The flip-flop 304 output 314 is connected as the microbubble signal 54 to the microprocessor 24 (FIG. 1) through a counter 305, preferably 82C54 IC, associated with the microprocessor 24. The counter 305 accumulates pulses proportional to the amount of time microbubble signals 54 are detected and makes that information 307 available as digital data to the microprocessor 24 (FIG. 1).

The isolation resistors 270, 280, 292, preferably 10 kΩ, at the input to each comparator isolates the common filtered signal 86 from each comparator 250, 252, 254, thus leaving the filtered signal 86 undisturbed in the event of a defective comparator input 272, 282, 294.

In the case of the control comparator circuit 94 (FIG. 2) the trouble signal 96 (FIG. 2) from the first comparator and the bubble signal 98 (FIG. 2) from the second comparator are connected together to form a single air signal 56 (FIG. 1) to the control microprocessor 26 (FIG. 1). With the outputs of both the comparators connected together a high-to-low logic swing would result if either comparator was activated. The air signal 56 is connected to the control microprocessor 26 (FIG. 1) through a D flip-flop latch (not shown) associated with the microprocessor 26 (FIG. 1), in the same manner as the bubble signal 52 is connected to the monitor microprocessor 24 (FIG. 1).

Under normal bubble-free conditions all of the voltage comparator circuits receive the same nominal 2.5 volt DC filtered signal 86. However, whenever a bubble passes through the tube 34 in the tubing holder 32 (FIG. 1), the voltage of the filtered signal 86 drops below 2.5 volts. Small bubbles with volumes of about 0.1 μL, cause the voltage of the filtered signal 86 to drop by about 12% or to about 2.2 volts. Larger bubbles, with volumes of about 8 μL, cause the voltage of the filtered signal 86 to drop by about 52%, which drops the voltage to less than 1.2 volts. Bubbles larger than about 15 μL in volume can cause the voltage of the filtered signal to drop to almost zero. The filtered signal 86 voltage would also drop to zero signal when the tube 34 (FIG. 1) is not installed into the tubing holder 32 (FIG. 1) or when there is no blood 36 (FIG. 1) in the tube 34.

When the filtered signal 86 is at 2.5 volts the output 262 of the first comparator 250 and the trouble signal 50 are at a logical high state, indicating no trouble in the bubble detector circuit 30; the output 264 of the second comparator 252 and the bubble signal 52 are at a logical high state indicating no large bubbles, and the output 266 of the third comparator 254 is at a logical low state. The logical low state of the third comparator 254 output holds the J input 302 of the J-K flip-flop 304 at a low logical state which in turn holds the non-inverting output 314 and microbubble signal 54 at a low logical state, indicating the absence of microbubbles.

The comparators will toggle whenever the filtered signal 86 deviates above or below the threshold voltage used by each comparator 250, 252, 254 circuit.

The first comparator 250 toggles whenever the filtered signal 86 swings higher than 2.8 volts causing the trouble signal 50 to go to a low logic state, indicating to the microprocessor 24 (FIG. 2) that equipment failure has occurred. Such a condition might occur if a component failed in the ALC circuit 88. For the control comparator circuit 94 (FIG. 2) the first comparator toggles when the filtered signal 86 voltage swings above 5 volts.

The second comparator 252 changes state when the ultrasound signal drops to 1.2 volts. That condition would occur when the plastic tubing was not installed into the sensor assembly, upon a failure occurring in the ALC circuit or when a large bubble is sensed. This causes the bubble signal 52 to go to a low logic state and indicating a bubble. The low logic state sets the D flip-flop latch 265 output 267 to a logical high state, signaling the monitor microprocessor 24 (FIG. 1) of the occurrence of the bubble. The flip-flop 265 stays set until reset 267' by the microprocessor 24 (FIG. 1).

When the filtered signal 86 drops below 2.2 volts the output 266 of the third comparator 254 goes to a logical high level indicating the presence of a microbubble. It is undesirable to shut down the artificial kidney apparatus 20 upon the occurrence of an isolated microbubble. The parameter of interest in the case of microbubbles is the volume of air per unit time, a maximum allowable of 1 cubic centimeter per minute delivered past the detector in the form of microbubbles in the preferred embodiment. A running average is therefore determined by the microprocessor 24 to determine when the number of microbubbles has reached a critical level. In the preferred embodiment of the artificial kidney apparatus 20 (FIG. 1) the microprocessors 24, 26 (FIG. 1) control the rate of blood flow through the tube. Whenever the third comparator 254 output goes to a high logical level a stream of clock pulses at a pulse frequency of 1.22 MHz is sent to the counter 305. The counter 305 accumulates the number of clock pulses and compares them to a time reference. The number of clock pulses counted would then be proportional to the length of time the small bubble comparators were activated. By frequently monitoring the number of pulses counted, and taking into account the rate of blood flow in the tube 34 (FIG. 1) the microprocessor 24 (FIG. 1) can ascertain the approximate volume air contained in the microbubbles. Thus the microprocessor 24 (FIG. 1) can determine the blood flow rate and compensate for the expected changes in bubble signals as the blood flow rate changes.

The J-K flip-flop 304 serves two functions. It provides a fast rise and fall time signal. It also turns on and off the timing signal 72 signal that is derived from the oscillator circuit 70. When triggered by the third comparator 254, the flip-flop 304 produces an output signal 314 that is ½ the frequency of the 2.45 MHz transducer clock signal. When the "J" input of the IC goes to a high logical value the flip-flop turns into a simple one bit counter. The 2.45 MHz clock signal that is connected to the clock input is therefore divided by two and emerges as a 1.22 MHz signal at the output 314 whenever the third comparator 254 is activated. The 1.22 MHz frequency is selected to be high enough so that substantially all detected microbubbles result in at least one clock pulse at all expected flow rates, yet low enough that the registers of the counter 305 are not filled between times when the microprocessor 24 (FIG. 1) reads the counter 307.

The method by which the microprocessors 24, 26 (FIG. 1) interpret the signals 50, 52, 54, 56, 58 (FIG. 1) from the bubble detector circuit 30 (FIG. 1) will be described by reference to FIGS. 11-13. Each microprocessor 24, 26 (FIG. 1) sequentially polls its associated signals 50, 52, 54, 56, 58 (FIG. 1) periodically, every 25 milliseconds in the preferred embodiment. Alternatively, the microprocessors 24, 26 (FIG. 1) could operate on an interrupt basis, processing the signals 50, 52, 54, 56, 58 (FIG. 1) from the bubble detector circuit 30 (FIG. 1) only when they change state.

Referring to FIG. 11, to interpret the trouble signal 50 (FIG. 10) from the first comparator 250 (FIG. 10) of the monitor comparator circuit 92 (FIG. 10) the monitor microprocessor 24 (FIG. 1) polls the trouble signal 50 (FIG. 10) to determine if a logical low state is present, indicating a failure as described above (at 500). If there is no failure indicated, a software trouble signal timer is reset to zero (at 502) and the poll of the trouble signal 50 (FIG. 10) is terminated (at 504) until the next polling cycle.

If the trouble signal 50 (FIG. 10) is at a logical low value the microprocessor 24 (FIG. 1) ascertains if a test of the trouble signal 50 (FIG. 10) function is in progress (at 506). If such a test is in progress, the monitor determines that the test has been passed (at 508) and terminates the poll of the trouble signal 50 (FIG. 10) (at 504) until the next polling cycle.

If, however, a test of the trouble signal 50 (FIG. 10) function is not in progress, the monitor microprocessor 24 (FIG. 1) reads the software trouble signal timer to determine if the timer has timed out (at 510). The trouble signal 50 (FIG. 10) may go momentarily to a logical low state under certain conditions not indicative of a failure, such as a filtered signal 86 (FIG. 10) voltage overshoot at the end of the passage of a large bubble through the tube 34 (FIG. 1). The software trouble timer prevents nuisance alarms by ensuring that a trouble state exists for a predetermined time, 1.5 sec in the preferred embodiment, before activating an alarm. The software timer is reset (at 502) when the trouble signal 50 (FIG. 10) returns to a logical high value, indicating no failure.

If the software trouble timer has not expired the timer is permitted to continue running and the poll of the trouble signal 50 (FIG. 10) is terminated until the next polling cycle. If, however, the software trouble timer has expired, a trouble alarm is activated (at 512), indicating UABD failure and the poll of the trouble signal 50 (FIG. 10) is terminated (at 504) until the next polling cycle. The trouble alarm may activate audible and visual alarm indications and may shut down the artificial kidney apparatus 20 (FIG. 1).

Referring to FIG. 12, to interpret the bubble signal 52 (FIG. 10) from the second comparator 252 (FIG. 10) of the monitor comparator circuit 92 (FIG. 10) the monitor microprocessor 24 (FIG. 1) polls the output 267 (FIG. 10) of the D flip-flop latch 265 (FIG. 10) to determine if a logical high state is present, indicating the passage of a large bubble through the tube 34 (FIG. 1) (at 520). If there is no large bubble indicated the poll of the D flip-flop latch 265 (FIG. 10), and thus the bubble signal 52 (FIG. 10), is terminated (at 522) until the next polling cycle.

If the output 267 (FIG. 10) of the D flip-flop latch 265 (FIG. 10) is at a logical low value the microprocessor 24 (FIG. 1) ascertains if a test of the bubble signal 52 function is in progress (at 524). If such a test is in progress, the monitor microprocessor 24 (FIG. 1) determines that the test has been passed (at 526), sends a reset signal 267' (FIG. 10) to the D flip-flop latch 265 (FIG. 10) (at 528) and terminates the poll of the output 267 (FIG. 10) of the D flip-flop latch 265 (FIG. 10), and thus the bubble signal 52 (FIG. 10) is terminated (at 522) until the next polling cycle.

If, however, a test of the bubble signal 52 (FIG. 10) function is not in progress, a bubble alarm is activated (at 530), indicating passage of a large bubble. The bubble alarm may activate audible and visual alarm indications and may shut down the artificial kidney apparatus 20 (FIG. 1). The poll of the D flip-flop latch 265 (FIG. 10), and thus the bubble signal 52 (FIG. 10), is terminated (at 522) until the next polling cycle.

The control microprocessor 26 (FIG. 1) polls and interprets the air signal 56 (FIG. 1) by the same method that the monitor microprocessor 24 (FIG. 1) uses to poll and interpret the bubble signal 52 (FIG. 1).

The interpretation of the microbubble signal 54 (FIG. 10) presents problems not present in interpreting the bubble signal 52. In particular, microbubbles may appear in a more or less continuous cluster of mutually indistinguishable microbubble, known as a "string-of pearls." The volume of air contained in such a string of pearls is a function of both the time that the string takes to pass through the tube 34 (FIG. 1) and the velocity at which it is moving. Since the parameter of interest is not the occurrence of a microbubble, but rather the volume of air in microbubble form per unit time to pass through the tube 34 (FIG. 1), it is necessary to account for these factors. The speed at which the microbubbles are moving is substantially determined by the blood flow rate, which is established by the microprocessor 24 (FIG. 1). The count accumulated in the counter 37 (FIG. 10) over a fixed period of time indicates the time a string of microbubbles takes to pass through the tube 34 (FIG. 1). By using this data it is possible to "split" "the string of pearls" and estimate the amount of air in the form of microbubbles per unit time to pass through the tube 34 (FIG. 1).

Referring to FIG. 13, to interpret the microbubble signal 54 (FIG. 10) from the third comparator 254 of the monitor comparator circuit 92 the monitor microprocessor 24 (FIG. 1) examines the value of the blood flow rate through the tube 34 (FIG. 1) (at 540). The microprocessor 24 (FIG. 1) then determines if the flow rate has changed since the last polling cycle (at 542). If the blood flow rate has changed the microprocessor 24 (FIG. 1) calculates a counts per microbubble factor, which is a constant divided by the blood flow rate (at 544). The constant is directly proportional to the pulse frequency and the assumed size of a microbubble. In the preferred embodiment, for blood flow rate units of mL per hour, a pulse frequency of 1.22 MHz and an assumed microbubble size 10 $\mu$L, the constant is approximately $44.1 \times 10^6$. The poll of the microbubble signal 54 (FIG. 10) is terminated (at 504) until the next polling cycle.

If the blood flow rate has not changed, the microprocessor 24 (FIG. 1) examines the microbubble counter 305 to ascertain the number of counts currently accumulated in the counter 305 (at 548). This value is compared to the value ascertained a predetermined time earlier, one minute in the preferred embodiment, and a difference calculated to ascertain the number of counts accumulated during the predetermined time period (at 550). The number of counts accumulated during the predetermined time period is then divided by the counts per microbubble to ascertain the number of microbubbles, and thus the total quantity of air in the form of microbubbles, to pass through the tube 34 (FIG. 1) during the predetermined time period (at 552). The number of microbubbles to pass through the tube during the predetermined time period is then compared to an allowable number of microbubbles or total quantity of air per unit time, 1 mL/min in the preferred embodiment (at 554). If the allowable limit has not been equalled or exceeded the poll of the microbubble signal 54 (FIG. 10) is terminated (at 546) until the next polling cycle.

If the allowable number of microbubbles or total quantity of air per unit time has been equalled or exceeded the microprocessor 24 (FIG. 1) ascertains if a test of the microbubble signal 54 (FIG. 10) function is in progress (at 556). If such a test is in progress, the monitor microprocessor 24 (FIG. 1) determines that the test has been passed (at 558) and terminates the poll of the microbubble signal 54 (FIG. 10) (at 546) until the next polling cycle.

If, however, a test of the microbubble signal 54 (FIG. 10) function is not in progress a microbubble alarm is activated (at 560), indicating UABD failure and the poll of the microbubble signal 54 (FIG. 10) is terminated (at 546) until the next polling cycle. The microbubble alarm may activate audible and visual alarm indications and may shut down the artificial kidney apparatus 20 (FIG. 1).

The control microprocessor 26 (FIG. 1) polls and interprets the control microbubble signal 58 (FIG. 1) by the same method that the monitor microprocessor 24 (FIG. 1) uses to poll and interpret the monitor microbubble signal 54 (FIG. 1).

In order to test the bubble detection function the control microprocessor 26 (FIG. 1) blocks the actuation of a bubble alarm and activates the control test signal line 62 (FIG. 9) for a predetermined period of time, 0.6 second in the preferred embodiment, turning on the control test FET 240 (FIG. 9) to emulate a bubble. The bubble and air signal interpreting functions described above then detect the signals and determine if the bubble detector circuit has passed the test.

The trouble function is tested by performing a test of the bubble function. At the end of the bubble function test a short duration filtered signal 86 (FIG. 10) voltage overshoot will occur which will cause the trouble signal 50 (FIG. 10) to go the a low logical value for a short period of time. Failure to detect the voltage overshoot indicates that the trouble function is faulty.

In order to test the microbubble function the monitor microprocessor 24 (FIG. 1) blocks the actuation of a microbubble alarm and sends a series of sixteen cycles of a one Hz square wave signal on the monitor test signal line 60 (FIG. 9), turning on the monitor test FET 238 (FIG. 9) intermittently to emulate sixteen microbubble occurrences. The microbubble signal interpreting function described above then detects the signals and determines if the bubble detector circuit has passed the test.

Failure of any of the tests activates an alarm. The alarm may activate audible and visual alarm indications and may shut down the artificial kidney apparatus 20 (FIG. 1).

The tubing holder 32 of the present invention will be described by reference to FIGS. 14 through 19. Referring to FIG. 14 the tubing holder 32 comprises a housing 320 into which the two transducer mounting blocks 38, 42 are retained. The housing is an elongated rectangular prism having a top 322, a bottom 324, a first end 326, a second end 328 and two sides 330, 332. A tubing acceptance slot 334 is formed into the top 322 of the housing, parallel to the sides 330, 332, centered between the sides, and extending from the first end 326 to the second end 328. The tubing acceptance slot 334 is defined by a semi-circular floor 336 having its lowest point approximately half way between the top 322 and the bottom 324 and two vertical planar sidewalls 338, 340 which extend upwardly from the floor and intersect the top to form two housing leading edges 342, 344. A 45 degree bevel is formed at each housing leading edge 342, 344.

Referring to FIG. 15, two generally rectangular mounting block receiving sockets 346, 348 are formed in the bottom 324 of the housing 320 located symmetrically on opposite sides of the tubing acceptance slot 334. Each receiving socket 346, 348 extends from the bottom 334 nearly to the top 322 of the housing 320. A stabilizer slot 350 is formed on each side of each receiving socket 346, 348. The distance between edges 352, 354 of the receiving sockets that are closest to each other is less than the width of the tubing acceptance slot 334. A rectangular window 356 is formed in each sidewall 338, 340 of the tubing acceptance slot 334 interconnecting the slot 334 with each of the mounting block receiving sockets 346, 348.

The housing 320 is machined of acetal plastic. The housing 320 may also be molded from plastic, preferably acetal plastic. Two brass threaded inserts 360 are formed in the bottom of the housing 320 along a central axis, each being proximate to an end 326, 328 of the housing, to provide a means of attaching the tubing holder 32 to a panel 361 (FIG. 18) of the artificial kidney apparatus 20.

Referring to FIG. 16, each mounting block 38, 42 comprises a body 362 in the shape of a rectangular prism having a top 364, a bottom 366, two sides 368, 370, a rear face 372 and a front tubing engagement face 374. A rectangular stabilizing flange 376 is formed along, and extends perpendicularly from, the bottom 366 and two sides 368, 370 of the body 362. Referring to FIG. 17 the tubing engagement face 374 has a leading edge 378 where it intersects the top 364 of the body 362, trailing edge 380 where it intersects the bottom 366 of the body and two side edges 382, 384 where it intersects the sides of the body. The tubing engagement face 374 is the same size as a corresponding window 356 of the housing 320. A tubing retaining groove 386 having an arcuate cross section and a predetermined depth is formed into the tubing engagement face 374 parallel to the leading edge 378. The leading edge 378 is beveled at approximately 45 degrees. Each side edge 382, 384 is beveled.

Referring to FIG. 18, a blind hole recess 388 is formed in the back of each mounting block 38, 42 with its floor proximate the tubing retaining groove 386. A transducer 40, 44 is inserted into the recess 388 and held in proximity with the tubing retaining groove 386 with conventional potting compound 389. The transducer electrical leads 390 extend from the back of the mounting block and connect to conductive studs 392 mounted through holes in a reduced thickness portion 394 of the stabilizer flange 376. The mounting blocks 38, 42 are preferably formed of acrylo-butyl styrene plastic.

The mounting blocks 38, 42 are inserted into corresponding mounting block sockets 346, 348 of the housing 320. The mounting blocks 38, 42 are oriented with the tubing engagement faces 374 facing each other and protruding through the windows 356 by a distance approximately equal to the predetermined depth of the tubing retaining grooves 386.

The side portions of the stabilizer flanges 376 engage the stabilizer slots 350 at each side of the mounting block receiving sockets 346, 348.

Referring to FIGS. 18 and 19, to insert a tube 34 into the tubing holder 32 the tube 34 is inserted in the tubing acceptance slot 334 by pressing against the beveled leading edges 342, 344, 378, of the housing 320 and the tubing engagement faces 374, compressing and deforming the tube 34. When the tube reaches the depth of the tubing retaining grooves 386 it returns to approximately its original shape, being compressed only slightly to promote secure retention of the tube 34 and coupling of the transducers 40, 44 to the tube 34. The tube 34 is thus retained in the tubing holder 32 until manually compressed and deformed for removal from the tubing retaining grooves 386 and thus the tubing acceptance slot 334.

A presently preferred embodiment of the present invention has been described with some particularity. It should be understood that this description has been made by way of preferred example and that the invention is defined by the scope of the following claims.

What is claimed is:

1. An inclusion detector for detecting the presence of inclusions in a flow of a liquid while compensating for changes in the detection environment comprising:
   a conduit;
   transmitting means for transmitting a signal through a liquid flowing in the conduit at a transmitted signal level;
   receiving means for receiving and interpreting the signal transmitted by the transmitting means, a change in a received signal level being indicative of the presence of an inclusion in the liquid flow; and
   signal adjusting means for adjusting the transmitted signal level to maintain an average value of the received signal level at a relatively constant value.

2. The inclusion detector defined in claim 1 wherein the inclusion is at least one bubble of at least one of air or gas.

3. The inclusion detector defined in claim 1 wherein the liquid is at least one of a biological or a pharmaceutical liquid.

4. The inclusion detector defined in claim 3 wherein the liquid is one of blood or a blood component.

5. The inclusion detector defined in claim 1 wherein the signal is an ultrasonic signal.

6. The inclusion detector defined in claim 5 wherein the conduit is flexible plastic medical tubing having a circumferential wall and the ultrasonic signals are transmitted and received through the wall of the tubing.

7. The inclusion detector defined in claim 5 wherein the transmitting means comprises:
   an oscillator; and
   a transmitting ultrasonic transducer electrically responsive to the oscillator.

8. The inclusion detector defined in claim 7 wherein the transmitting means further comprises a driver electrically responsive to the oscillator, the ultrasonic transducer being electrically responsive to the driver.

9. The inclusion detector defined in claim 8 wherein the adjusting means adjusts a level of voltage supplied to the driver to maintain a relatively constant voltage level at a predetermined point within the receiving means.

10. The inclusion detector defined in claim 9 wherein the driver comprises:
    a first transistor; and
    a second transistor; and
    the first and second transistors are electrically responsive to the oscillator to alternately apply and remove the voltage supplied to the driver to and from the transmitting transducer.

11. The inclusion detector defined in claim 7 wherein the receiving means comprises:
    a receiving ultrasonic transducer;
    a rectifier electrically responsive to the receiving transducer; and
    at least one signal comparator electrically responsive to the rectifier.

12. The inclusion detector defined in claim 11 wherein the receiving means further comprises:
    am amplifier electrically responsive to the receiving ultrasonic transducer, the rectifier being electrically responsive to the amplifier; and
    a filter electrically responsive to the rectifier, the at least one signal comparator being electrically responsive to the filter.

13. The inclusion detector defined in claim 12 wherein the level adjusting means adjusts the transmitted signal to maintain an average voltage level between the filter and the at least one comparator at a relatively constant value.

14. The inclusion detector defined in claim 11 further comprising:
    another signal comparator substantially identical to the at least one comparator and electrically responsive to the rectifier.

15. The inclusion detector defined in claim 11 wherein the at least one signal comparator comprises:
    a first signal comparator electrically responsive to the rectifier to detect the presence of a failure of the inclusion detector;
    a second signal comparator electrically responsive to the rectifier to detect the presence of a relatively large inclusion; and
    a third signal comparator electrically responsive to the rectifier to detect the presence of a relatively small inclusion.

16. The inclusion detector defined in claim 11 wherein the signal adjusting means further comprises:
    an integrator electrically responsive to the rectifier; and
    a supply voltage adjusting means electrically responsive to the integrator.

17. The inclusion detector defined in claim 1 wherein the inclusion is a solid particle.

18. The inclusion detector defined in claim 1 wherein the signal is a light signal.

19. A method for detecting the presence of inclusions in a liquid flowing in a conduit while compensating for changes in the detection environment comprising:

transmitting a signal through the liquid at a transmitted signal level;

receiving the signal at a received signal level;

interpreting the signal to detect the presence or absence of an inclusion, a sudden change in the received signal level being indicative of the presence of an inclusion; and adjusting the transmitted signal level to maintain the received signal level at a relatively constant level.

20. The detecting method defined in claim 19 wherein the inclusion is at least one bubble of at least one of air or gas.

21. The detecting method defined in claim 19 wherein the liquid is at least one of a biological or a pharmaceutical liquid.

22. The detecting method defined in claim 21 wherein the liquid is one of blood or a blood component.

23. The detecting method defined in claim 19 wherein the signal is an ultrasonic signal.

24. The detecting method defined in claim 23 wherein the conduit is flexible plastic medical tubing having a circumferential wall and the ultrasonic signals are transmitted and received through the wall of the tubing.

25. The detecting method defined in claim 23 wherein the transmitting step comprises:

generating an oscillating signal; and electrically driving a first ultrasonic transducer with the oscillating signal to produce ultrasonic mechanical vibrations.

26. The detecting method defined in claim 25 wherein the transmitting step further comprises amplifying the oscillating signal by a determined gain factor before the oscillating signal electrically drives the ultrasonic transducer.

27. The detecting method defined in claim 26 wherein the adjusting step comprises determining the determined gain of the amplifying step to maintain a relatively constant value of a voltage level that is proportional to the received signal level.

28. The detecting method defined in claim 25 wherein the receiving step comprises:

mechanically driving a second ultrasonic transducer with the ultrasonic mechanical vibrations produced by the first ultrasonic transducer to produce an electrical signal; and rectifying the electrical signal to produce a rectified electrical signal.

29. The detecting method defined in claim 28 wherein the receiving step further comprises:

amplifying the electrical signal before it is rectified; and filtering the rectified electrical signal to produce a filtered electrical signal.

30. The detecting method defined in claim 29 wherein the level adjusting step comprises adjusting the strength of the ultrasonic mechanical vibrations produced by the first ultrasonic transducer to maintain the average level of the filtered electrical signal at a relatively constant value.

31. The detecting method defined in claim 30 the signal adjusting step means further comprises:

integrating the value of the filtered electrical signal to produce an integrated electrical signal; and adjusting the strength of the ultrasonic mechanical vibrations produced by the first ultra sonic transducer in response to the integrated electrical signal.

32. The detecting method of claim 29 wherein the interpreting step comprises comparing the filtered electrical signal to at least one predetermined reference signal.

33. The detecting method defined in claim 32 wherein the interpreting step further comprises:

comparing the filtered electrical signal to a first predetermined reference signal to detect the presence of a relatively large inclusion; and comparing the filtered electrical signal to a second predetermined reference signal to detect the presence of a relatively small inclusion.

34. The detecting method defined in claim 19 wherein the signal is a light signal.

35. The detecting method detector defined in claim 19 wherein the inclusion is a solid particle.

36. An extracorporeal blood processing apparatus comprising:

a conduit for conveying blood;

transmitting means for transmitting an ultrasonic signal through the blood conveyed in the conduit at a transmitted signal level;

receiving means for receiving and interpreting the ultrasonic signal transmitted by the transmitting means, a relatively sudden change in a received signal level being indicative of the presence of at least one bubble of at least one of air or gas in the blood; and signal adjusting means for adjusting the transmitted signal level to maintain an average value of the received signal level at a relatively constant value.

37. The processing apparatus defined in claim 36 comprising a dialysis apparatus.

38. A tubing holder for retaining flexible tubing in contact with at least one ultrasonic transducer comprising:

a first mounting block;

a first generally planar tubing engagement face having an axis and a first leading edge generally parallel to the axis;

a first tubing retaining groove recessed into the first tubing engagement face, the first tubing engagement groove being generally parallel to the axis and spaced a predetermined distance from the leading edge and having a generally arcuate cross sectional configuration;

a first ultrasonic transducer mounted in the first mounting block below and in proximity with the first tubing retaining groove;

a second mounting block;

a second generally planar tubing engagement face having an axis and a second leading edge generally parallel to the axis;

a second tubing retaining groove recessed into the second tubing engagement face, the second tubing engagement groove being generally parallel to the axis and spaced a predetermined distance from the leading edge and having a generally arcuate cross sectional configuration; and a housing securing and supporting the first and second mounting blocks in a relationship wherein:

the first tubing engagement face faces the second tubing engagement face, is generally parallel to the second tubing engagement face and is spaced a predetermined distance from the second tubing engagement face;

the first leading edge is generally parallel to and opposite the second leading edge;

the first tubing retaining groove is generally parallel to and opposite the second tubing retaining groove; and the predetermined distance is selected to permit the tubing to be inserted between the first tubing engagement face and the second tubing engagement face at the location of the first and second leading edges when the tubing is relatively greatly compressed, and retained in the first and second tubing retaining grooves when the tubing is relatively less compressed.

39. The tubing holder defined in claim 38 further comprising a second ultrasonic transducer mounted in the second mounting block below and in proximity with the second tubing retaining groove at a location generally opposite the location of the first ultrasonic transducer.

40. The tubing holder defined in claim 38 wherein the leading edges are beveled.

41. A method for measuring the amount of air in the form of microbubbles in a liquid flowing in a tube comprising:

transmitting a signal through the liquid at a transmitted signal level;

receiving the signal at a received signal level;

interpreting the signal to detect the presence or absence of a microbubble, a change in the received signal level being indicative of the presence of a microbubble;

generating at least one logic signal pulse for each microbubble detected:

counting the number of logic pulses generated over a predetermined time period;

establishing the number of logic signal pulses that represent one microbubble and ascertaining the number of microbubbles in the tube during the predetermined time period; wherein:

the logic pulses are generated at a predetermined frequency during a detection time period when a microbubble is detected; and the establishing step comprises:

determining a value of a constant that is directly proportional to the frequency at which the logic pulses are generated and directly proportional to an expected microbubble size; and dividing the constant by a flow rate of the liquid in the tube.

42. The method defined in claim 42 wherein the ascertaining step further comprises:

dividing the number of logic pulses counted over the predetermined time period by the number of logic pulses that represent one microbubble.

43. The method defined in claim 41 further comprising:

correlating the number of microbubbles ascertained in the predetermined time period with a volume of air in the flowing liquid during the predetermined time period.

44. The method defined in claim 41 further comprising:

comparing the number of microbubbles ascertained in the predetermined time period with an allowable number of microbubbles for the time period.

45. The method defined in claim 41 further comprising:

activating an alarm if the number of microbubbles ascertained in the predetermined time period exceeds the allowable number of microbubbles for the time period.

* * * * *